(12) United States Patent
Campbell et al.

(10) Patent No.: US 8,586,387 B2
(45) Date of Patent: Nov. 19, 2013

(54) METHODS OF TRIGGERING ACTIVATION OF ENCAPSULATED SIGNAL-GENERATING SUBSTANCES AND APPARATUS UTILISING ACTIVATED SIGNAL-GENERATING SUBSTANCES

(75) Inventors: Neil J. Campbell, Damascus, MD (US); Keith Edward Moravick, Mountain View, CA (US); Joseph D. Penniman, Soquel, CA (US); Bruce J. Richardson, Los Gatos, CA (US)

(73) Assignee: Supernova Diagnostics, Inc., Germantown, MD (US)

( * ) Notice: Subject to any disclaimer, the term of this patent is extended or adjusted under 35 U.S.C. 154(b) by 138 days.

(21) Appl. No.: 13/221,600

(22) Filed: Aug. 30, 2011

(65) Prior Publication Data
US 2013/0052749 A1 Feb. 28, 2013

(51) Int. Cl.
*G01N 33/543* (2006.01)

(52) U.S. Cl.
USPC ........... 436/518; 436/501; 436/536; 436/155; 436/172; 424/1.25; 424/1.29

(58) Field of Classification Search
USPC .................. 436/155, 172; 424/1.25, 1.29
See application file for complete search history.

(56) References Cited

U.S. PATENT DOCUMENTS

2009/0325171 A1\* 12/2009 Hirt et al. ........................ 435/6
2012/0156693 A1\* 6/2012 Wong et al. ................... 435/7.9

FOREIGN PATENT DOCUMENTS

| GB | 2470939 A | 12/2010 |
| WO | WO 02/12888 A2 | 2/2002 |
| WO | WO 2004/087308 A1 | 10/2004 |
| WO | WO 2010142960 A1 * | 12/2010 |

OTHER PUBLICATIONS

Green et al., Assay for fluorescein diacetate hydrolytic activity: Optimization for soil samples, 2006, Soil Biology and Biotechnology, vol. 38, pp. 693-701.*
Further Search Report under Section 17 for GB1120357.7 dated Aug. 20, 2012 by Dr. Jonathan Corden of Intellectual Property Office.

* cited by examiner

*Primary Examiner* — Melanie Y Brown
*Assistant Examiner* — Erik B Crawford
(74) *Attorney, Agent, or Firm* — RatnerPrestia

(57) ABSTRACT

A method of performing a bioassay comprising activating capsules containing a signal precursor that is hydrolysable from a latent form in which substantially no signal is generated to a form in which it is able to generate a detectable signal, said activating comprising treating said capsules with heat and with an acid or a base catalysing solution, the combination of said heat and the pH of the catalysing solution being such as to hydrolyse said precursor to the form in which it is able to generate a detectable signal.

24 Claims, 21 Drawing Sheets

METHODS OF TRIGGERING ACTIVATION OF ENCAPSULATED SIGNAL-GENERATING SUBSTANCES AND APPARATUS UTILISING ACTIVATED SIGNAL-GENERATING SUBSTANCES

The present invention relates to bioassays, e.g., for detecting bacterial contamination in food, for detecting biological pollutants in water, or for detecting the presence of substances such as antibodies, antigens and nucleic acids in body fluids such as blood and its components, nasopharyngeal fluids, urine or saliva. The material that it is desired to detect is often generally called the target or analyte.

In particular, the invention is concerned with bioassays that use an encapsulated signal generating substance for indicating the presence of the target in a sample (qualitative) or for determining the amount of target present in a sample (quantitative) and to methods for controlling the onset of signal generation from capsules containing a signal precursor material that is convertible from a latent form in which substantially no signal is generated to a form in which it is able to generate a detectable signal. More particularly, the invention is concerned with controlling the release of the signal precursor material from the capsules and controlling its conversion from its latent form to the signal generating form. In the description which follows, this process will be referred to as "triggering activation".

BACKGROUND OF THE INVENTION

Bioassays are based on the interaction of at least one labelled biomolecule with an analyte (target) to be detected. The label acts as a marker indicating that a reaction has taken place between the target and a purposely chosen receptor or affinity molecule on the biomolecule that exclusively interacts with and binds to the target. The label can be measured using different techniques:
  (i) optically by the measurement of the absorption of a dye or the fluorescent light emitted by fluorophores, or the luminescent light emitted by luminescent or chemiluminescent compounds, or measurement of turbidity caused by the light scattering of agglutinated latex particles;
  (ii) radioactively by the measurement of radio isotopes;
  (iii) electrochemically by the measurement of mediators or electroactive substances;
  (iv) magnetically by the measurement of magnetic force; or.
  (v) piezoelectrically by the measurement of changes in mass.

Well known labels include enzymes as used in enzyme-linked immunosorbent assays (ELISAs) and radio isotopes used in radioimmunoassay; other label types include fluorophores, luminophores, chromophores, liposomes, latex particles in immuno agglutination assays, dyes, mediators, and gold particles.

The present invention is particularly, though not exclusively, concerned with labels that are detectable using optical techniques and with controlling the onset of maximum signal output so that readings can be taken and, if desired, repeated during a time period before the signal output decays or before the signal becomes dissipated through dilution and/or diffusion.

The purpose of the capsules in the present invention is two-fold: firstly, they serve as a vehicle or substrate for affinity molecules or receptors that are attached on the capsule surface and that are selected for their ability to specifically recognise and bind to a target molecule in a sample. Secondly, the capsules contain many molecules ($10^7$ to $10^9$ or higher) of the signal precursor. Consequently, upon binding between a target molecule with one of the affinity molecules on a capsule surface and upon subsequent conversion of the signal precursor within the capsule from its latent form to its signal generating form, the presence of a single target molecule can be indicated by many tens of millions or even thousands of millions of detectable signal generating molecules. This is a very powerful amplification technique that can extend the limits of detection of a bioassay.

Capsules containing an organic signal-generating substance for use in bioassays are known from published international patent application no. WO02/12888 A2, the disclosure of which is incorporated herein by reference in its entirety. These known capsules are prepared by treating an uncharged solid organic signal-generating substance that has low water solubility or that is water insoluble (such as fluorescein diacetate (FDA)) with an aqueous solution of an amphiphilic substance (e.g., ionic detergent), The amphiphilic substance arranges itself on the surface of the solid signal-generating substance, imparting an electrical charge to its surface and rendering it susceptible to subsequent coating with a layer of a charged polyelectrolyte, followed by multiple alternating layers of oppositely charged polyelectrolytes. Polymer layers self-assemble onto the solid signal-generating substance (with its induced charge from the amphiphilic substance) by means of electrostatic layer-by-layer deposition, thus forming a multilayered polymeric shell around the solid core.

The coating step can also be carried out using a single layer of a substance bearing functional groups for covalent coupling of the coating layer, not using electrostatic deposition.

The thus-obtained capsules are modified for use in a bioassay by having affinity molecules attached to their surface, the affinity molecules being selected according to the type of target molecule that is to be detected.

In a first step of a detection method using the above-described capsules, a solution of target molecules is incubated with capsules modified with affinity molecules that specifically recognise the target molecules. The incubation is carried out over a time period sufficient to result in a target-affinity molecule complex; the affinity molecule remains bound to the capsule.

In a second step of the detection method, the resulting target-affinity molecule-capsule complexes are separated from capsules whose affinity molecules have not formed complexes with target molecules.

In a third step of the detection method, the capsules are disintegrated to release the signal-generating organic substance into solution, for example by treating them with an organic solvent such as an alcohol, a ketone, an ester, an ether, etc.

In the final step of the detection method, the signal that is generated by the released and dissolved signal-generating organic substance is detected and measured. The detected signal is related to the amount of the target molecules.

However, one of the disadvantages of this known detection method is that the disintegration of the capsules and the generation of the signal by the signal-generating organic substance is generally slow and can take varying amounts of time. This is undesirable because, in a lateral flow test using a liquid permeable membrane or a test using microfluidic channels, for example, the signal generating molecules are released into a solvent stream that is undergoing lateral flow. Hence, slow release of the signal generating molecules can lead to a detectable signal that is diffuse because it is spread by the flow of solvent.

SUMMARY OF THE INVENTION

Methods have now been discovered for controlling the release of the signal precursor from within the capsules and for controlling conversion of the signal precursor from its latent form to its signal generating form in a short time period. A signal maximum is achieved within in a few seconds, enabling readings to be taken (and repeated if necessary) whilst the signal is at its peak value and before the signal strength wanes or the signal becomes dissipated through diffusion or dilution.

The methods are applicable to signal precursors that are convertible by acid- or base-catalysed hydrolysis from the latent form to the signal generating form. The key feature is to subject the capsules (actually, the capsule/affinity molecule/target complexes) to a treatment solution having a balanced pH that is just too high for significant acid-based hydrolysis to occur or, in the alternative, just too low for significant base-catalysed hydrolysis to occur, and then to subject the treatment solution to a burst of heat to achieve a treatment solution temperature in the range from 45° C. to 65° C. This accelerates the reaction kinetics, triggering activation of signal generation: the signal precursor is hydrolysed from its latent form to its signal-generating form and becomes detectable in the solution as a bright signal. In some circumstances, it may be sufficient if the generated signal is detected by the naked eye. For example, a strong signal that is detectable by the naked eye may be sufficient for a qualitative test for indicating that a target or analyte is present in a sample. In other circumstances, it may be desirable to detect the amount of signal generated for a quantitative determination of the amount of target or analyte present in a sample. In this case, detection of the signal may be performed electronically using a reader device.

In a lateral flow or microfluidic test in accordance with the present invention, the maximum signal is generated sufficiently quickly that no diffusion or dissipation effects interfere with reading of the signal. Also, the treatment solution prior to heating is able to maintain the capsules in a stable form for a sufficient length of time for the reactants and reagents to flow along the test strip membrane or microfluidic channels as intended before the triggering activation step is implemented.

An embodiment of the present invention improves the reaction kinetics, enabling results to be obtained more quickly. The signal output is manageable and controllable by the user. In an embodiment, the maximum signal output is achieved almost immediately. This means that readings can be completed almost immediately and repeat readings can be taken before the signal output begins to degrade.

In an embodiment, the invention provides a method of triggering the generation of a signal generation in a bioassay using capsules containing a signal precursor that is hydrolysable from a latent form in which substantially no signal is generated to a form in which it is able to generate a detectable signal. The method comprises treating the capsules with a treatment solution whose pH and temperature are such that no significant hydrolysis of the signal precursor takes place and then heating the capsules in the treatment solution to initiate onset of hydrolysis of the signal precursor to the form in which it is able to generate a detectable signal.

At the balanced pH and temperature, the signal precursor is stable but hydrolyzes when heated. Ultrasonic vibration may be used to effect heating, as well as more traditional forms of heating.

Another embodiment of the invention provides apparatus for performing a bioassay using capsules containing signal precursor that is hydrolysable from a latent form in which substantially no signal is generated to a form in which it is able to generate a detectable signal. The apparatus includes means for heating an ambient temperature balanced pH solution containing the capsules.

Another embodiment of the invention provides apparatus for detecting a signal output from a bioassay device that uses capsules containing a signal precursor that is hydrolysable from a latent form in which substantially no signal is generated to a form in which it is able to generate a detectable signal, the apparatus comprising:

(i) a light source for illuminating a reaction zone where the capsules are treated with a solution his temperature is such that substantially no hydrolysis of the signal precursor takes place and whose pH is balanced such that either:

(a) the pH is too high for the signal precursor to undergo significant acid-catalysed hydrolysis at ambient temperature but at which the signal precursor undergoes significant hydrolysis at elevated temperature;

or:

(b) the pH is too low for the signal precursor to undergo significant base-catalysed hydrolysis at ambient temperature but at which the signal precursor undergoes significant hydrolysis at elevated temperature;

(ii) an optical detector for detecting light emitted from the bioassay device, and (iii) a heating device for heating solution in the reaction zone to a temperature at which the signal precursor undergoes hydrolysis.

In yet another embodiment of the invention, there is provided a method of performing a bioassay using capsules containing a signal precursor that is convertible from a latent form in which it emits substantially no signal to a form which is capable of generating a detectable signal, wherein the detection step includes treating the capsules with an ambient temperature balanced pH solution and then heating the solution to cause conversion of the signal precursor from its latent form to its signal generating form.

DETAILED DESCRIPTION

Figure 1:
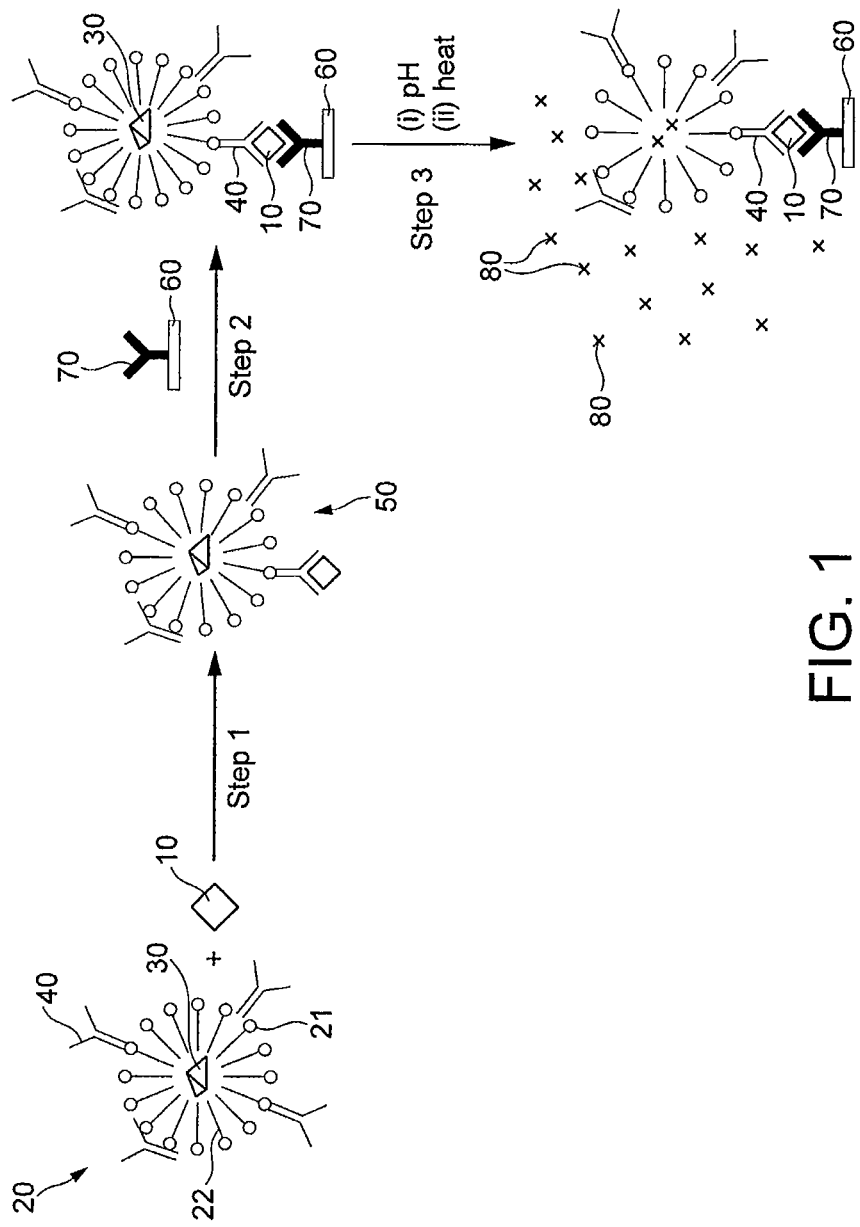
FIG. 1 is a schematic representation of a bioassay detection method in accordance with an embodiment of the present invention for detecting a target molecule (analyte) using encapsulated signal precursor molecules.

Referring to FIG. 1, this shows a schematic representation of the steps of an example of a bioassay detection method according to an embodiment of the present invention using labelled capsules to bind with a target molecule or analyte, the capsules containing a signal precursor that is convertible to a signal generating form that is released from the capsules.

Step 1—Formation of Complexes Between Target Molecules and Affinity Molecules on Capsule Surface In the first step, a test sample suspected of containing the analyte 10 is mixed in solution with capsules 20 containing signal precursor material 30. The walls of the capsules may, for example, be formed from lipids having hydrophobic heads 21 and hydrophilic tails 22. The capsules have affinity molecules 40 on their surfaces that are chosen for their ability to interact specifically with the analyte and to bind with it. The analyte, if present, will become bound to the capsules via the intermediary of the affinity molecules to form complexes 50.

Step 2—Immobilisation of Complexes

In the second step, the complexes 50 are immobilised on a substrate 60 which has capture molecules 70 attached to its surface. The capture molecules 70 are also chosen for their ability to bind specifically with the analyte 10, so capsules that have not become bound to analyte will not interact with the capture molecules 70 and will not become immobilised. Immobilised complexes form a "sandwich" at the immobilisation site, comprising immobilised capture molecule 70, analyte 10, and affinity molecule 40 (that remains attached to the capsule 20).

Step 3—Conversion of Signal Precursor to Signal Generating Form—Triggering Activation In the third step, the immobilised complexes are treated in a treatment solution to convert the signal precursor 30 to its signal generating form in which individual signal generating molecules 80 are released from the capsules into solution for detection by signal detection means (not shown).

According to an embodiment of the present invention, this third step is carried out by treating the immobilised complexes to a heating step in a balanced pH solution. A balanced pH solution is one in which the pH is slightly too high for the signal precursor to undergo acid-catalysed hydrolysis to its signal generating form, or one in which the pH is slightly too low for the signal precursor to undergo base-catalysed hydrolysis to its signal generating form. The capsules are stable in the balanced pH treatment solution and the signal precursor contained in the capsules does not undergo any appreciable amount of hydrolysis. However, when additional heat is applied, the reaction kinetics are altered and hydrolysis of the signal precursor takes place to convert it to its signal generating form.

In an alternative embodiment of the present invention, where little or no interval is required between addition of the treatment solution to the immobilised complexes and the onset of hydrolysis (activation triggering), a strongly acidic or strongly basic treatment solution can be used and no heating step is necessary.

Experimental Determination of Activation Triggering of Encapsulated Signal Precursor Under Different pH and Temperature Conditions Referring now to FIGS. 2 to 5, the experimental setup will be described that was used to evaluate the triggering of activation for encapsulated signal precursor under different conditions of pH and temperature.

Figure 2:
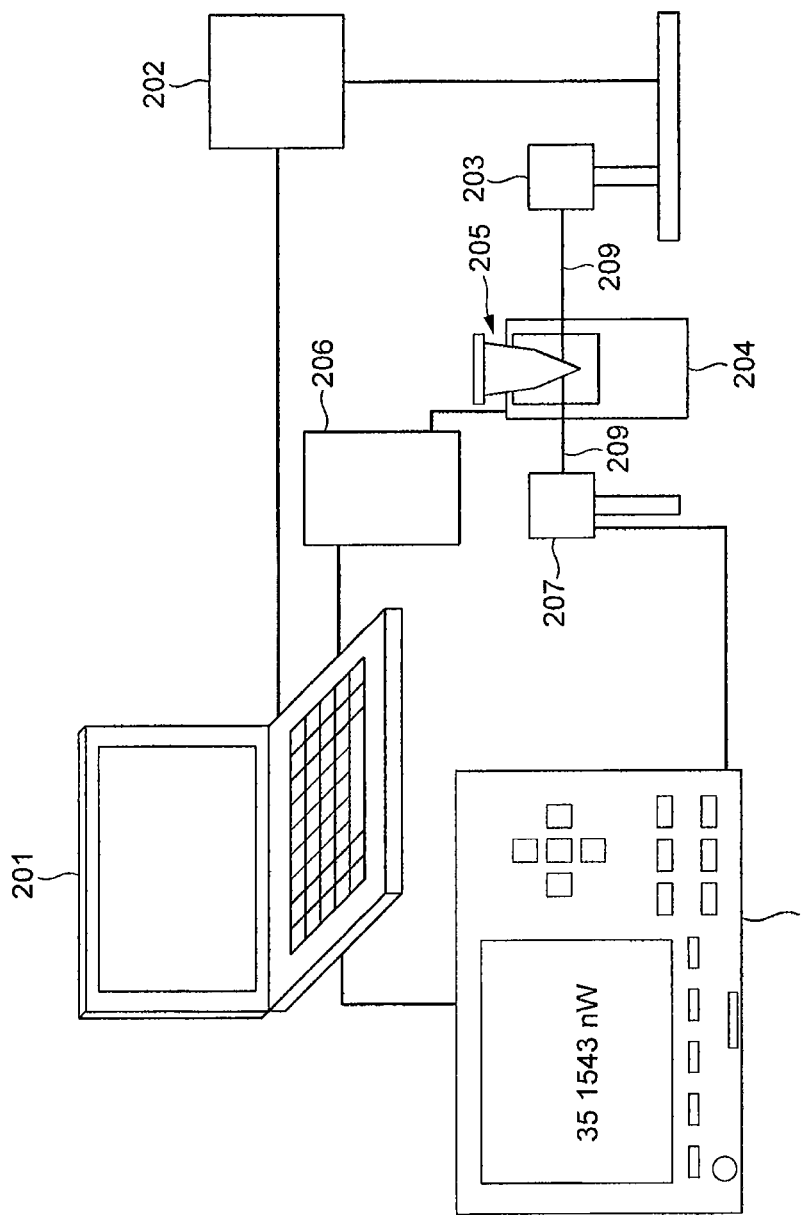
FIG. 2 is a schematic representation of the experimental apparatus used for investigating the triggering of activation of encapsulated signal precursor under different pH and temperature conditions.

FIG. 2 is a schematic illustration of the overall experimental setup, which comprises a computer 201 for controlling the experiments, a data acquisition board 202, an excitation light source 203 feeding excitation light via optical fibre 209 to a sample to be tested contained in a sample tube 205 placed in a temperature controlled tube holder 204. A temperature controller 206, under the control of computer 201, regulates the temperature of the tube holder 204. A second optical fibre 209 feeds the emitted light to a detector 207 and optical power meter 208 converts the detected emitted light to a numerical readout that is fed back to the computer 201.

Figure 3:
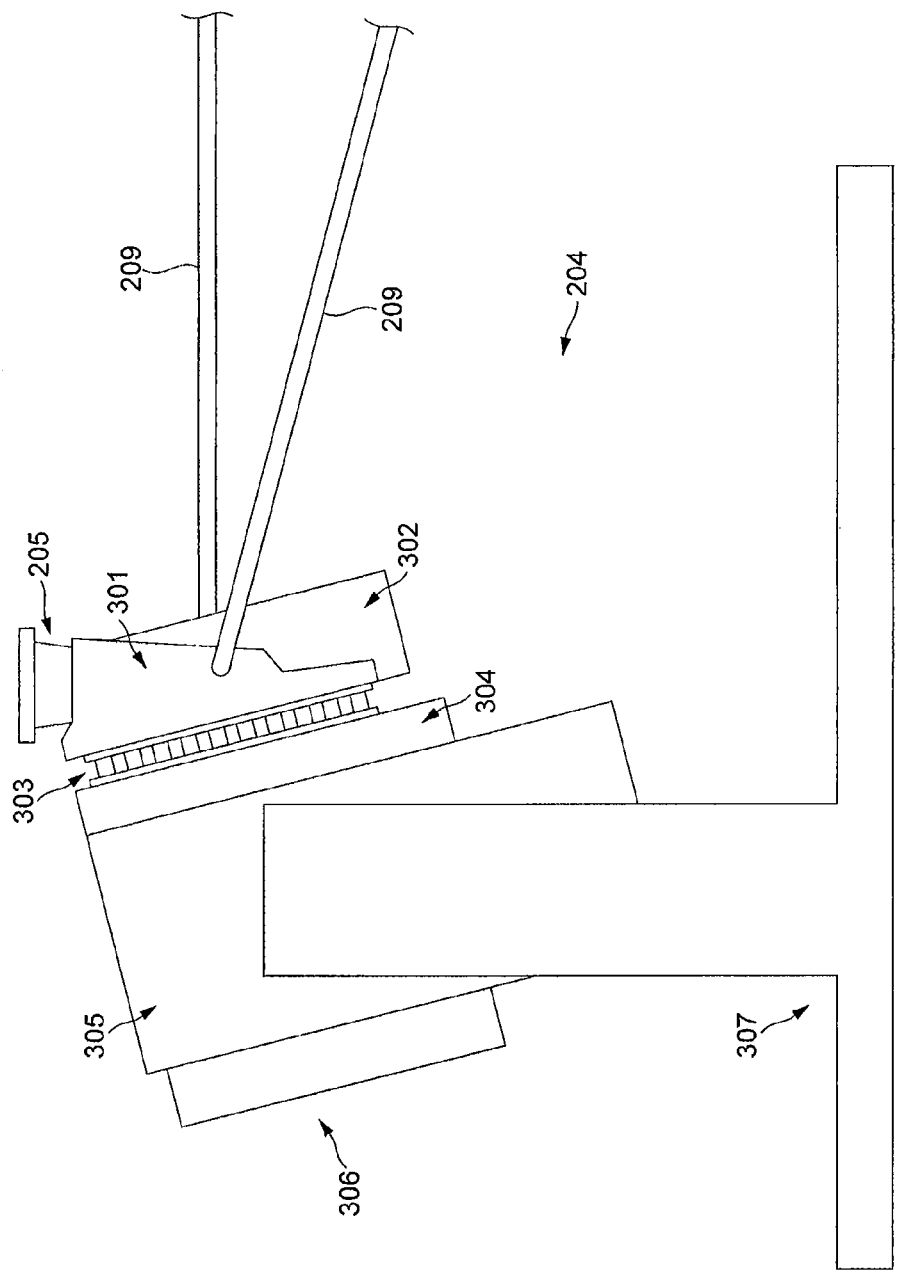
FIG. 3 is a schematic illustration of part of the experimental apparatus depicted in FIG. 2, showing detail of a temperature controlled sample tube holder.

FIG. 3 is a schematic illustration showing detail of the temperature controlled sample tube holder 204. The tube holder comprises a thermal block 301 into which the sample tube 205 is insertable, and an insulating block 302. At the rear of the thermal block 301 there is a Peltier device 303 used for heating the sample in the tube 205. The thermal block 301 transfers heat from the Peltier device 303 to the sample in the tube 205; the insulating block 302 insulates the system, preventing heat from escaping from the assembly and preventing outside ambient air from adding or removing heat. Peltier device 303 is mounted on a cold plate 304 having cooling fins 305. Forced cooling may be provided by a fan 306. The temperature controlled tube holder assembly is mounted on a heat sink stand 307.

Figure 4:
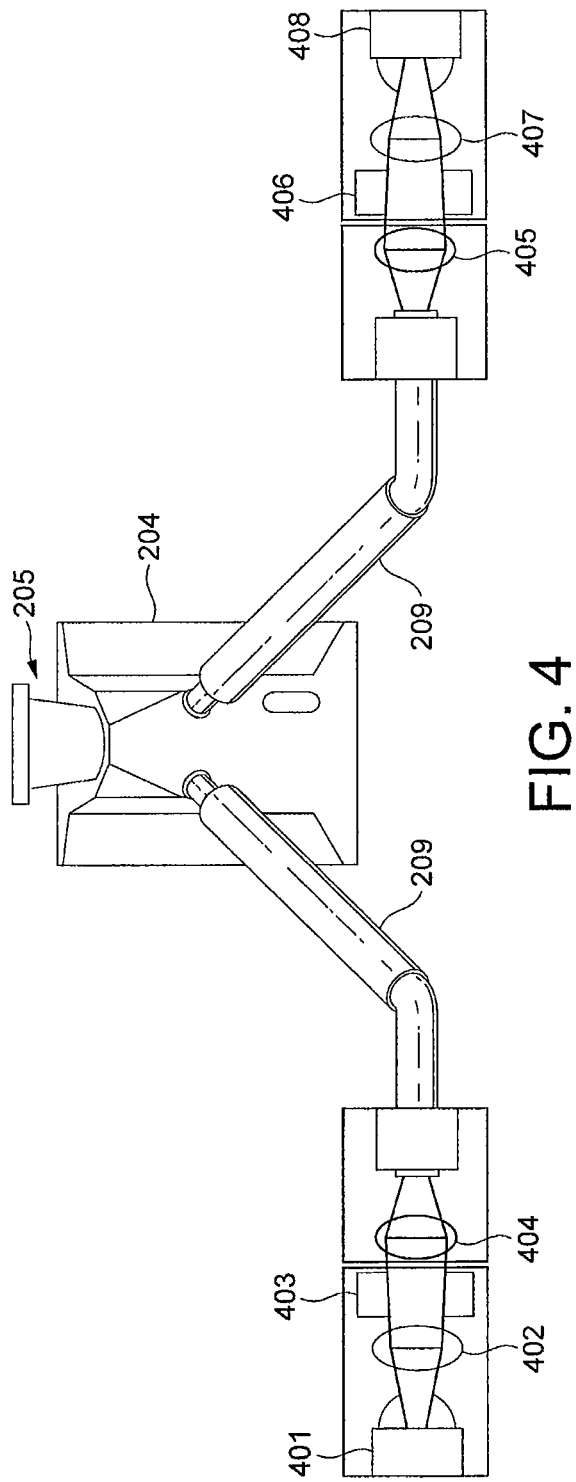
FIG. 4 is a schematic illustration of part of the experimental apparatus depicted in FIG. 2 showing the coupling of an excitation light source to the temperature controlled sample tube holder and the coupling of a photodiode detector to the tube holder.

Referring now to FIG. 4, the optical setup will be described. The temperature controlled tube holder 204 is equipped with two optical fibres 209 that are substantially at right angles to each other and in a plane oriented nearly perpendicular to the long axis of the tube 205 when it is positioned in the holder. One of the optical fibres 209 is connected to a filtered light source 401 which may be, for example, an LED. The light from source 401 passes through a collimating lens 402, then through an excitation filter 403 that filters out wavelengths that do not contribute to excitation of the signal generating molecules whose activation is to be triggered, and through a coupling lens 404 to the optical fibre 209. The second optical fibre is for transmitting emitted light from the sample tube 205 to an optically filtered high sensitivity optical power meter (208, see FIG. 2) for measuring the amount of light emitted from the excited molecules in the sample tube. Light from this second optical fibre 209 passes through a collimating lens 405, then through an emission filter 406 that filters out unwanted emission wavelengths, and through focusing lens 407 to photodiode 408. Both excitation filter 403 and emission filter 406 are 10 nm wide bandpass filters.

The following parts were used in constructing the experimental apparatus:

Temperature controller—tube and solution heating (TE Tech, model: TC-36-25-RS232)
24V DC Power Supply (Mean Well, model: SP-320-24)
Data Acquisition Device (Measurement Computing, model: USB-1280FS)
High power LED driver (Luminus model: DK-114N-3)
Detector Head (Newport Corp., model: 918D)
Optical Fibers (PVC jacketed, 1000 um core, NA=0.50)
Peltier Module (TE Tech, model: TE 63-1.0-1.3)
Resistor network to adjust voltage to Peltier device
Fiber Coupled LED Head (customized to maximize coupling)
Temperature Controlled Tube Holder:
a. Fiber adapter block (customized to maximize insulation)
b. Thermal tube block (customized to minimize thermal mass)
c. Heat exchange assembly (cold plate, fins, fan)
Light tight cover The apparatus was shrouded under the light tight cover (not shown) when experiments were carried out.

As described above, the temperature controlled tube holder 204, the excitation light source 203 and the optical power meter 208 are each connected to computer 201 that controls when the heat is applied, when the excitation light is turned on and when the optical power meter collects emission data.

At commencement of each experiment, a known volume of a pH adjusted activation solution was placed into a microcentrifuge tube serving as the sample tube 205 which was in turn placed into temperature controlled tube holder 204. The computer collected a continuous stream of emission data from the tube containing only activation solution. This provided a baseline for the circumstances where no signal precursor and no signal generating molecules are present.

When a steady baseline was established, a known quantity of a solution of capsules containing fluorescein diacetate (FDA) as the signal precursor was dispensed into the tube 205 containing the temperature controlled activation solution. The solution of capsules was at the same temperature as the activation solution in the sample tube 205 in the tube holder 204. Fluorescein diacetate is non-fluorescent, but is hydrolysable to fluorescein which fluoresces strongly under excitation.

The computer 201 then began a cycle of taking a "dark" read of the emitted light with no excitation, then turning on the excitation light and taking a read of the excited fluorescence. The logged data contained three pieces of information: cycle number, dark read, and fluorescent excitation read.

Each cycle was 1 second long. Each read consisted of an average of 1000 individual samples of the collected light incident on the photodiode 408 of the optical power meter 208. This cycle continued throughout the heating experiment. After a certain number of cycles (representing a desired time delay), and without breaking the cycle, the computer 201 turned on the Peltier heater 303 which raised the temperature of the reaction volume to its elevated set-point within seconds. Once the heater had been turned on and the temperature raised to the desired level, the temperature was held constant for the remainder of the experiment. Data was logged continuously throughout the experiment.

When the capsules were introduced into the activation solution, some hydrolysis occurred and a process of auto-luminescence and self quenching began. The baseline of the light output from the solution increased, and the detector current went up from approximately $10^{-11}$ amps to $10^{-9}$ amps and then stayed fairly constant until heat was applied.

During the 'semi-stable'/'time-delay', phase of the experiment, readings of detected light during excitation were always higher than the dark read light levels logged at the same time. This difference was attributed to two causes:

(i) A small amount of excitation light passes through the emission filter 406. This happens when some of the excitation light gets coupled into the emission collection fiber 209. Despite having three decades ($10^3$) of light rejection outside of the emission filter's pass-band, this excitation light is detected.

(ii) When excited, some of the fluorescein released during the initial hydrolysis event fluoresces beyond the ability of the solution to self-quench. This fluorescence is detected.

Regardless of which reading is used (excited or non-excited), there is a direct correlation between the amount of fluorescein in solution, and the amount of light detected through the emission filter. It is a well known phenomenon that fluorescein self-quenches, i.e., adsorbs its own fluorescence, because of its wide excitation band. The decrease in the detected light once the heat was applied shows that, when the concentration of fluorescein increases, the solution's ability to self-quench also increases. This will be explained in more detail below with reference to FIG. 5.

Characteristics of Heat Activation Experimental Data

Figure 5:
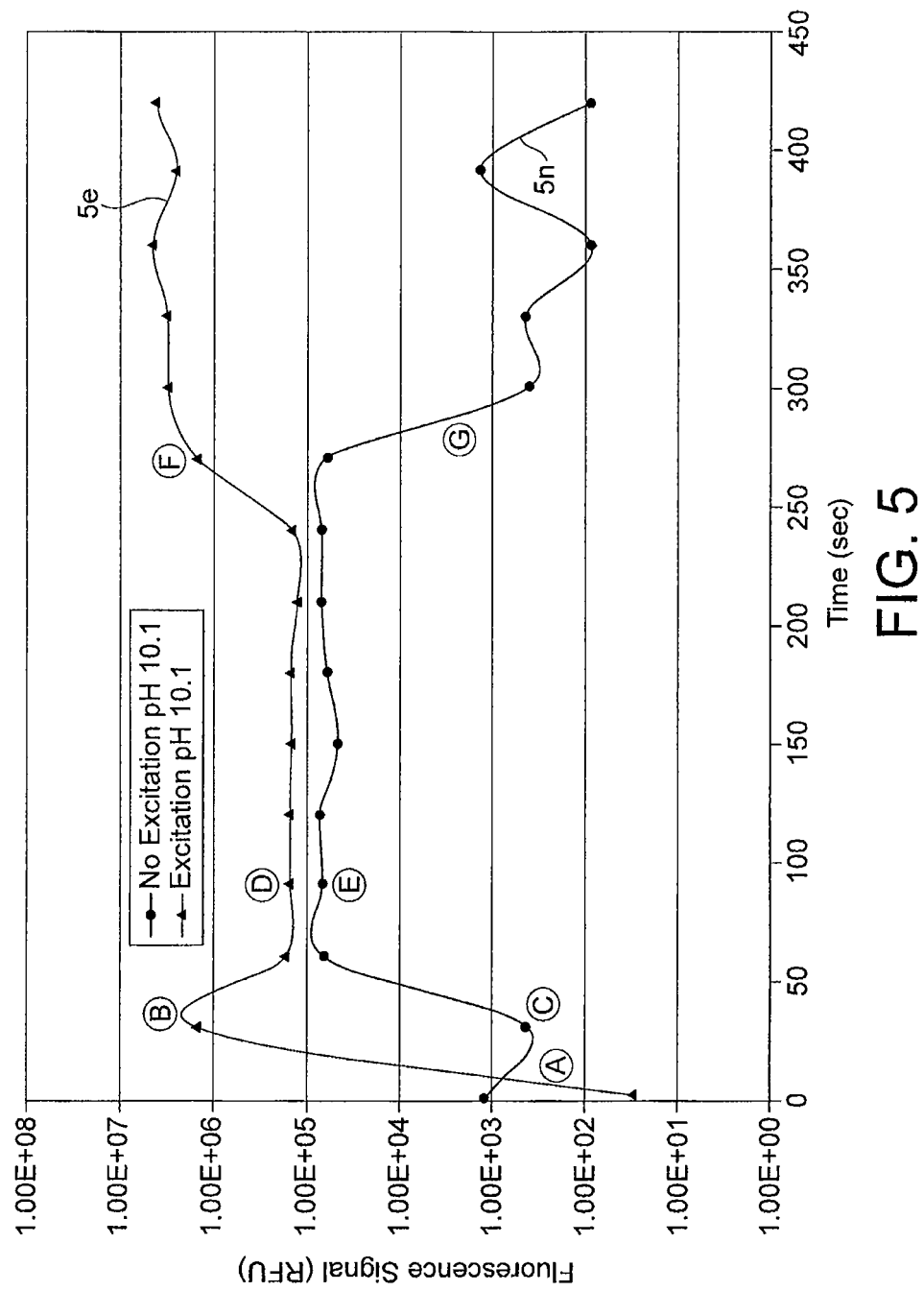
FIG. 5 is a graph showing various characteristics of the heat activation experimental data for fluorescein diacetate (FDA) in capsules in a basic treatment solution having a pH of 10.1 (just below the value required for hydrolysis of FDA to fluorescein)

FIG. 5 is a graph showing typical traces for light output from capsules formed from the lipid DSPE-PEG2000 Amine and sodium dodecyl sulfate (SDS) and containing FDA as the signal precursor. The capsules were placed in an activation solution having a pH of 10.1, which is just below the pH value at which FDA in this type of capsule will undergo hydrolysis to fluorescein without additional heat. In the following description, the behaviour at points A to G will be explained.

A. At time zero, the capsules were added to a room temperature activation solution of pH 10.1. Within seconds, an amount of fluorescein was released into solution.

B. In the excitation curve 5e, a rapid increase of fluorescein in solution during the first 30 seconds produced a burst in detected fluorescence that was actively quenched by under-excited neighboring fluorescein molecules.

C. In the non-excitation curve 5n, a simultaneous increase in self quenching reduced the detectable auto-luminescence. The total detectable luminous output of the solution headed towards a semi-stable equilibrium. Over time this baseline increases even without the addition of heat.

D. In the excitation curve 5e, the baseline value recorded during excited reads is always fractionally higher than reads taken with no excitation light. Without wishing to be bound by theory, this is thought to be due in part to two factors:
(a) Detectable excitation light leakage through the emission filter
(b) A small amount of detectable stimulated fluorescent emissions.

E. In the non-excitation curve 5n, this is the baseline value of detectable auto-luminescence that is not self-quenched.

F. In the excitation curve 5e, there is a detectable increase in fluorescence output due to hydrolysis of the FDA in the capsules upon application of heat to raise the temperature to 65° C. (Total Light=Stimulated Fluorescence+Autoluminescence−Selfquenched).

G. In the non-excitation curve 5n, there is a detectable increase in self quenching of auto-luminescence due to a rapidly increasing concentration of fluorescein in solution. (Total Light=Autoluminescence−Selfquenched).

Activation Triggering Under Different Conditions

Referring now to FIGS. 6 to 9, these are a series of graphs showing the behaviour of FDA-containing capsules formed from DSPE-PEG2000 Amine and sodium dodecyl sulfate (SDS), as used in the FIG. 5 evaluation described above.

Figure 6:
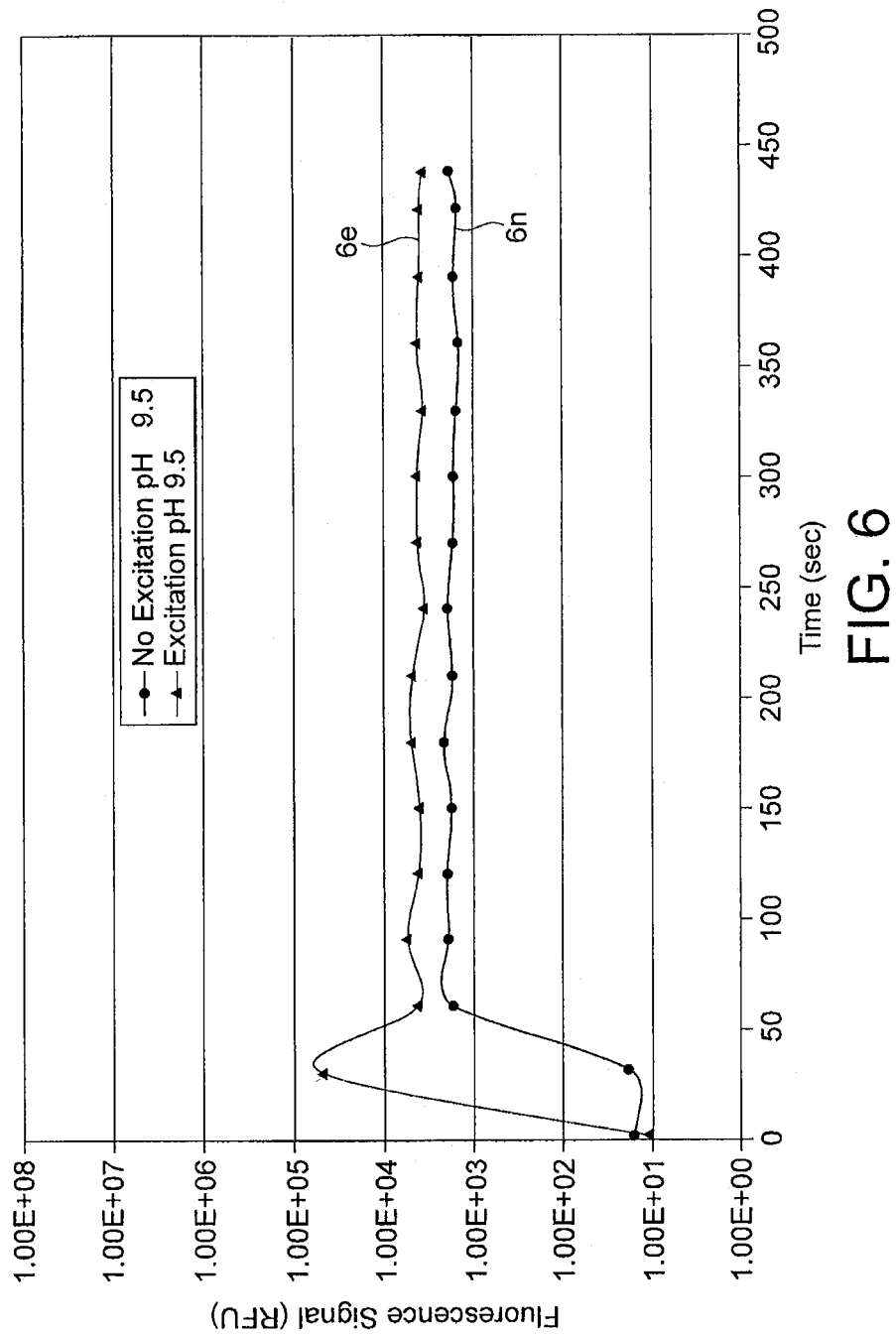
FIGS. 6 to 9 are further graphs showing the effects of different temperatures and different pH values on the activation of FDA to fluorescein in basic treatment solutions for capsules of a first type.

FIG. 6 is a graph showing the light output from the capsules in a treatment solution having a low pH value of 9.5 to which heat was applied after 250 seconds to raise the temperature of the treatment solution from room temperature (23° C.) to 45° C. No activation occurred; the excitation curve 6e and the non-excitation curve 6n continue their substantially parallel traces after the heat application. The capsules are stable at 45° C. at pH 9.5.

Figure 7:
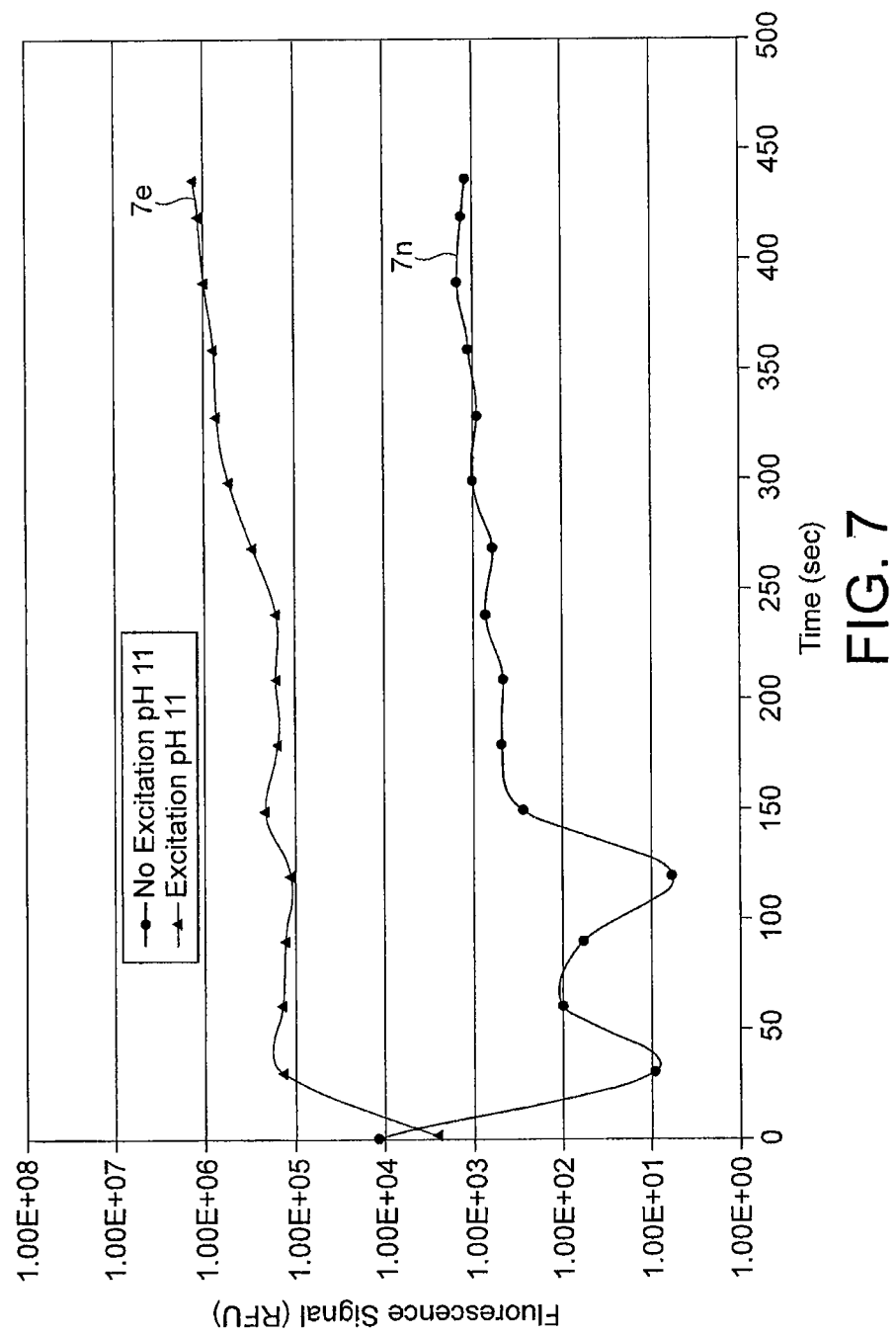

FIG. 7 is a graph showing the light output from the capsules in a treatment solution having a high pH value of 11.0. As before, the solution temperature was increased from room temperature (23° C.) to 45° C. after 250 seconds, but the high pH causes onset of activation almost immediately upon addition of the capsules to the solution and prior to the heating step. The excitation curve 7e and the non-excitation curve 7n are widely separated after about 25 seconds.

Figure 8:
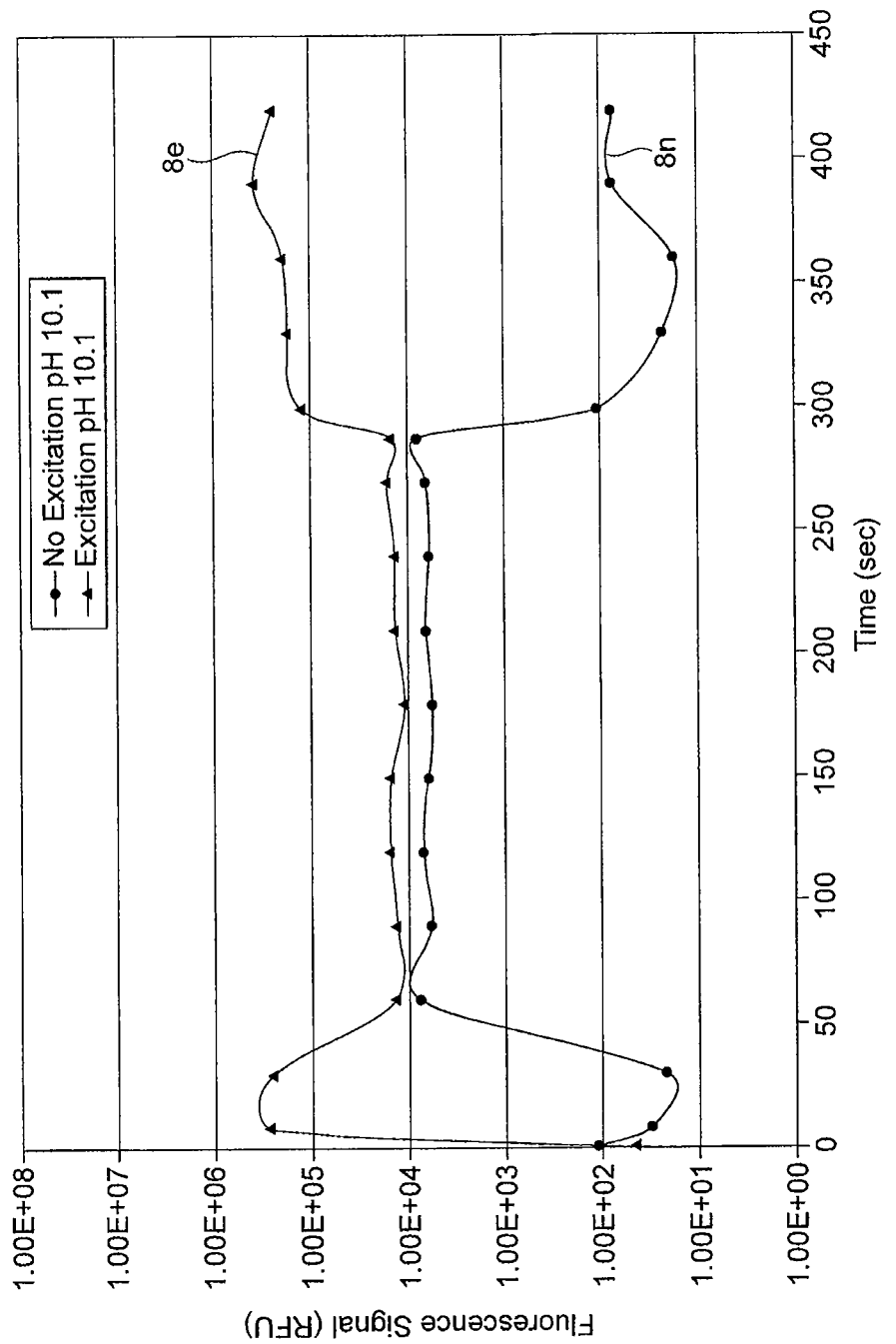

FIG. 8 is a graph showing the light output from the capsules in a balanced treatment solution having a pH value of 10.1 to which heat was applied after 300 seconds to raise the temperature of the treatment solution from room temperature (23° C.) to 65° C. Strong activation occurred upon heating. The excitation curve 8e and the non-excitation curve 8n are close together during the time period from 50 seconds to 300 seconds after addition of the capsules to the treatment solution. This demonstrates that the capsules are stable under these pH conditions at room temperature, but that activation can be triggered by heat.

Figure 9:
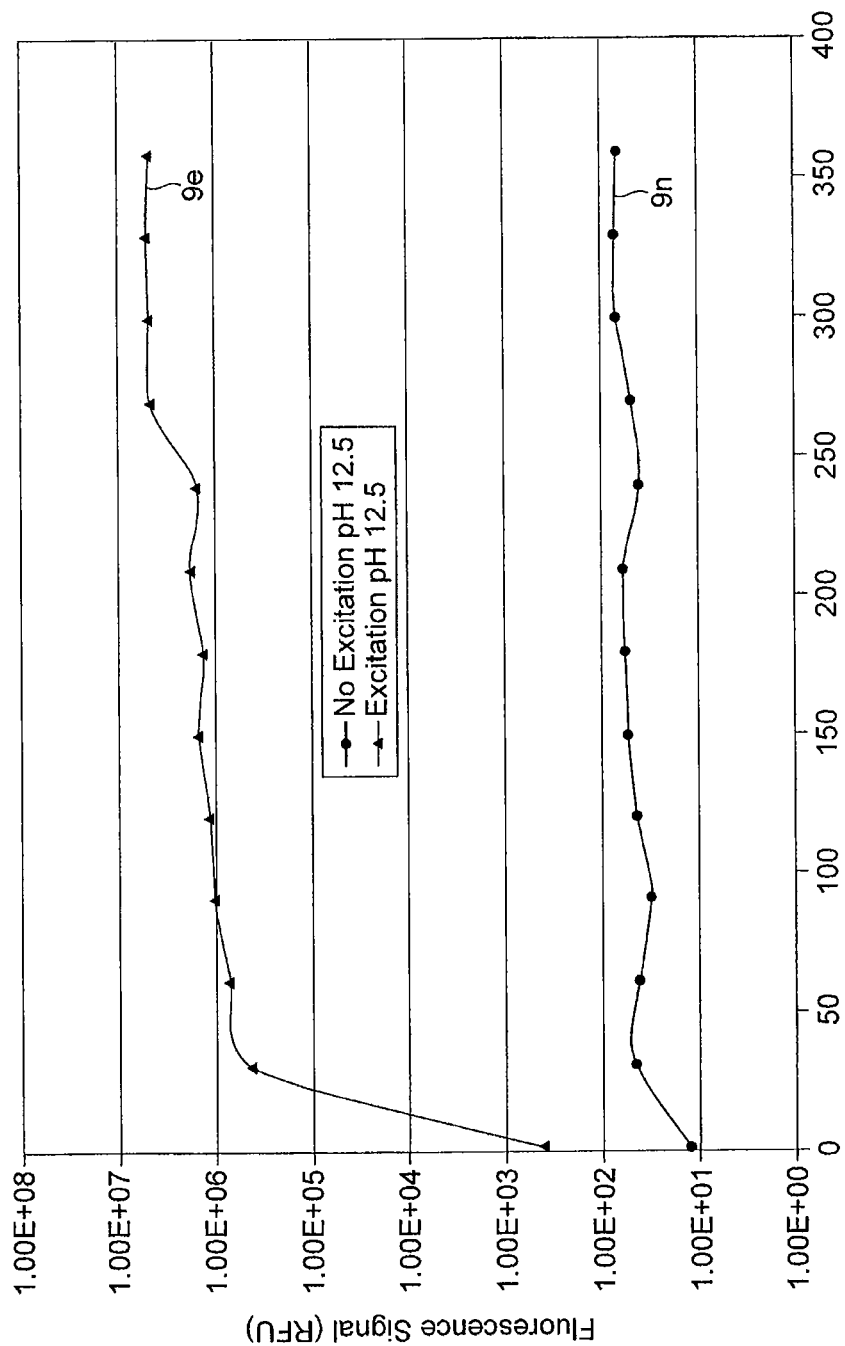

FIG. 9 is another graph showing the light output from the capsules in a treatment solution having a high pH value; in this experiment, the pH was 12.5. After 250 seconds, the solution temperature was increased from room temperature (23° C.) to 65° C., but the high pH caused onset of activation almost immediately upon addition of the capsules to the solution and prior to the heating step. The excitation curve 9e and the non-excitation curve 9n are widely separated after about 25 seconds and, although a slight increase in the fluorescent output can be seen in excitation curve 9e after the temperature was raised at 250 seconds, this is not a significant increase. This experiment demonstrated that high pH can be used on its own to trigger activation without delay. This may be useful in circumstances where immediate activation is desirable and a period of stable equilibrium before triggering of activation is not required.

Referring now to FIGS. 10 to 13, these are a series of graphs showing the behaviour of a different type of FDA-containing capsules under specified pH and temperature conditions. This batch of FDA-containing capsules was prepared using layer-by-layer deposition of polyelectrolytes as described in published international patent application no. WO02/12888 A2.

Figure 10:
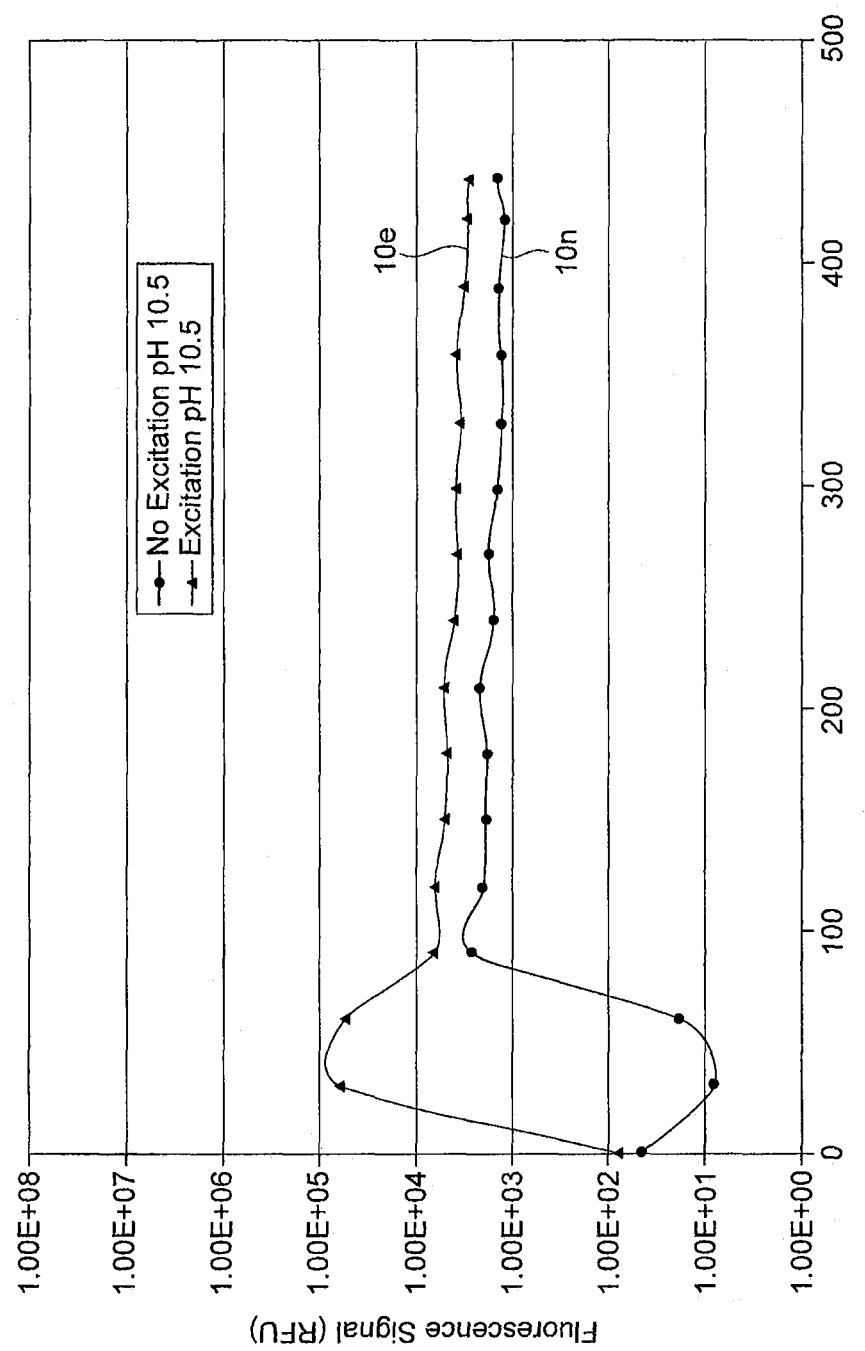
FIGS. 10 to 13 are graphs showing the effects of different temperatures and different pH values on the activation of FDA to fluorescein in basic treatment solutions for capsules of a second type.

FIG. 10 is a graph showing the light output from the capsules in a treatment solution having a low pH value of 10.5 to which heat was applied after 250 seconds to raise the temperature of the treatment solution from room temperature (23° C.) to 45° C. No activation occurred; the excitation curve 10e and the non-excitation curve 10n continue their substantially parallel traces after the heat application. These capsules are stable at 45° C. at pH 10.5.

Figure 11:
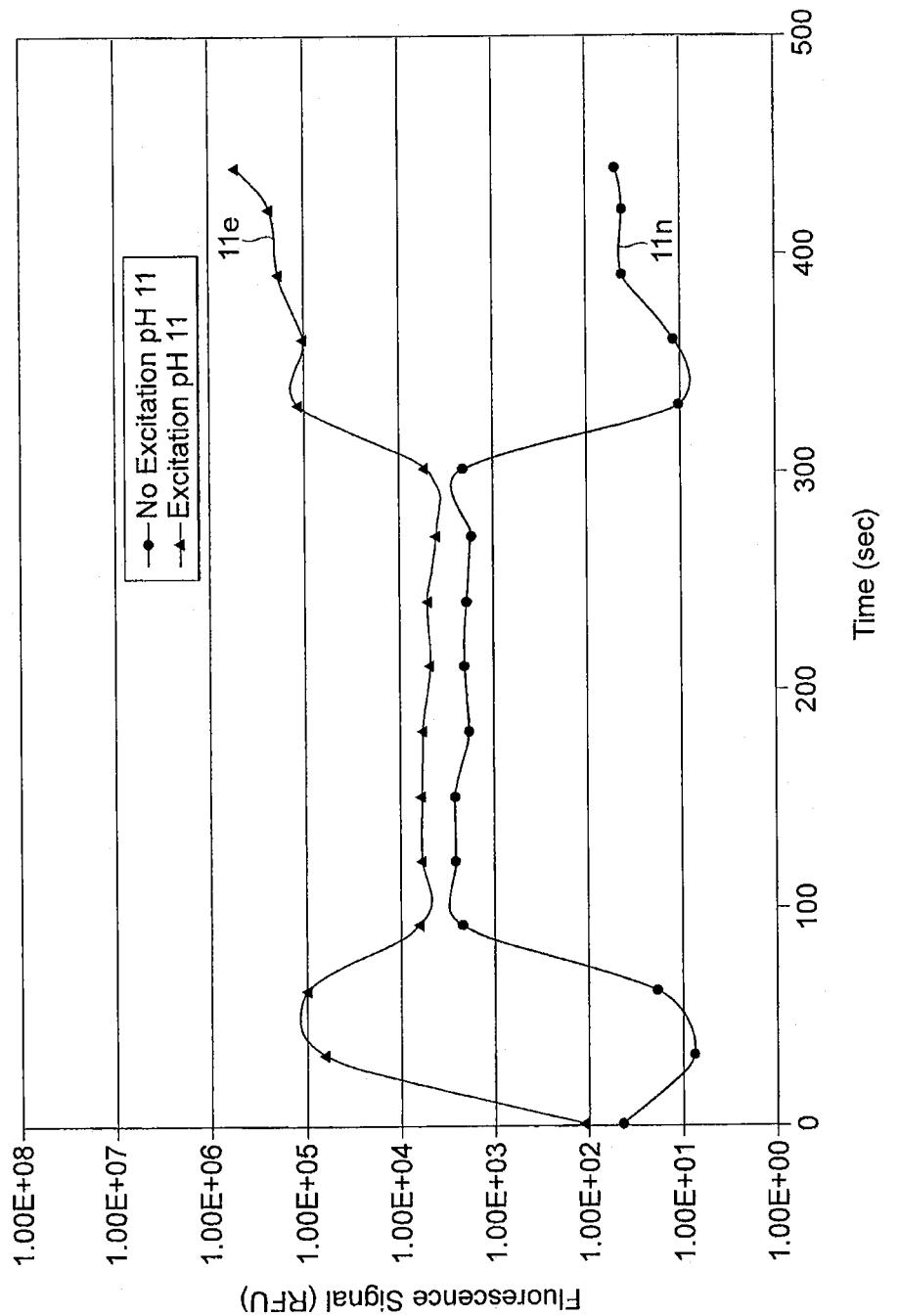

FIG. 11 is a graph showing the light output from the capsules in a balanced treatment solution having a pH value of 11 to which heat was applied after '300 seconds to raise the temperature of the treatment solution from room temperature (23° C.) to 45° C. Strong activation occurred upon heating. The excitation curve 11e and the non-excitation curve 11n are close together during the time period from about 75 seconds to 300 seconds after addition of the capsules to the treatment solution. This demonstrates that the capsules are stable under these pH conditions at room temperature, but that activation can be rapidly triggered by only moderate heat.

Figure 12:
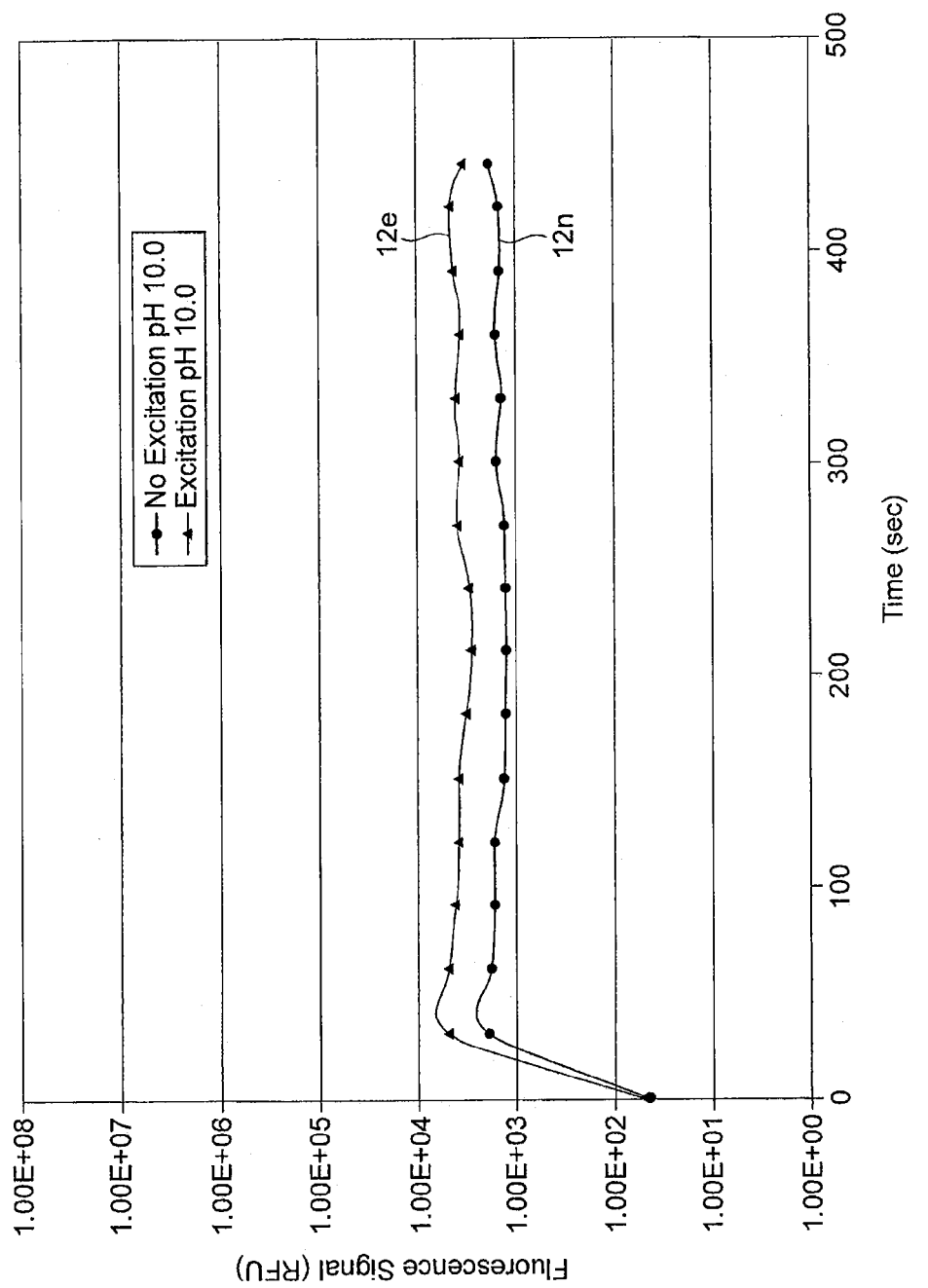

FIG. 12 is a graph similar to that of FIG. 10, showing the light output from the capsules in a treatment solution having an even lower pH value of 10.0 but to which more heat was applied after 250 seconds to raise the temperature of the treatment solution from room temperature (23° C.) to 65° C. Again, no activation occurred; the excitation curve 12e and the non-excitation curve 12n remain close together and continue their substantially parallel traces after the heat application. These capsules are stable at pH 10.0 even at 65° C.

Figure 13:
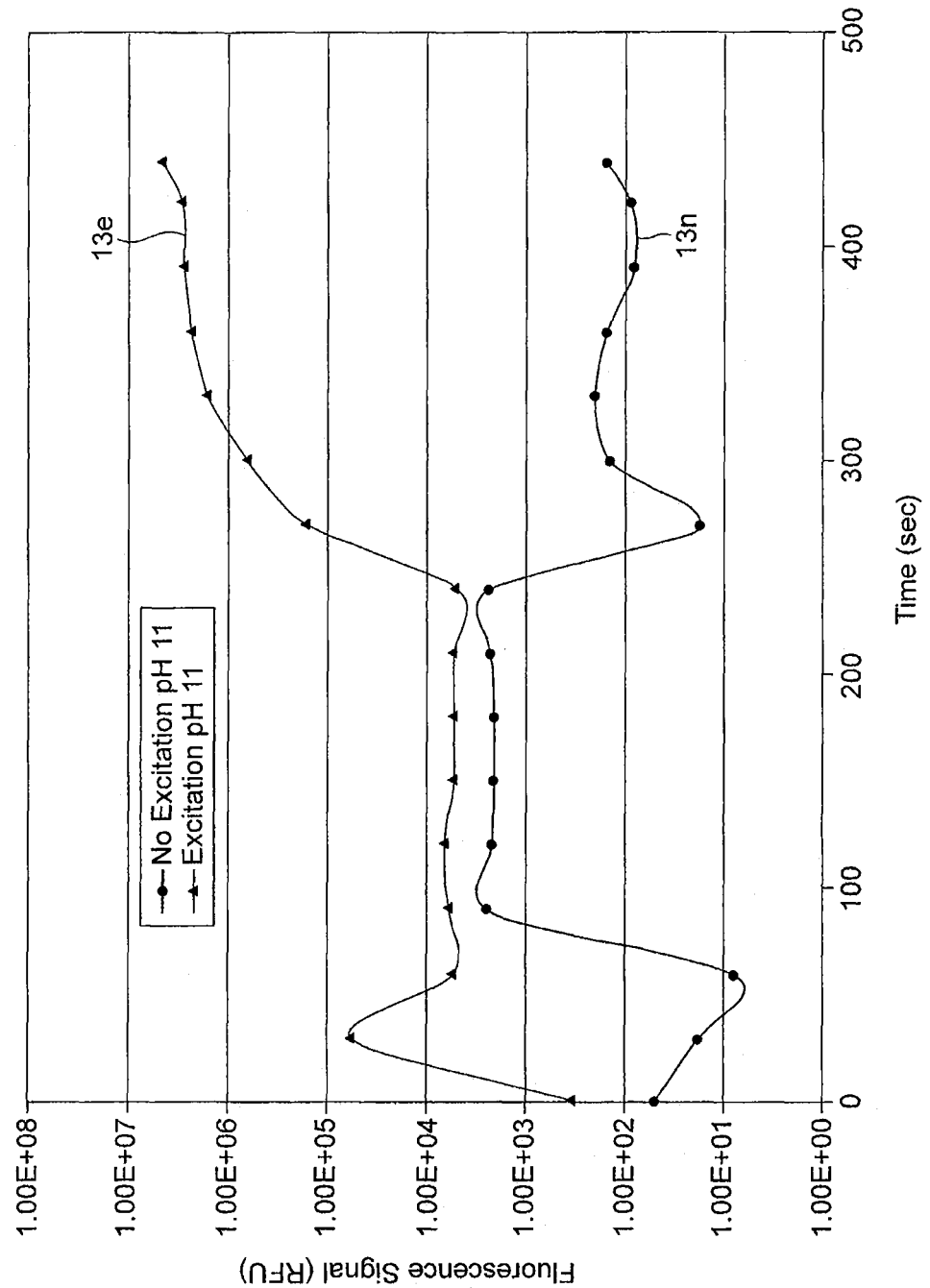

FIG. 13 is a graph similar to that of FIG. 11 showing the light output from the capsules in a balanced treatment solution having a pH value of 11, to which heat was applied after 250 seconds to raise the temperature of the treatment solution from room temperature (23° C.) to 45° C. Strong activation occurred upon heating. The excitation curve 13e and the non-excitation curve 13n are close together during the time period from about 75 seconds to 250 seconds after addition of the capsules to the treatment solution. This demonstrates that the capsules are stable under these pH conditions at room temperature, but that activation can be rapidly triggered by heat.

This experiment also demonstrates that the triggering of activation is caused by the temperature increase. Heat was applied 50 seconds earlier in this experiment than in the FIG. 11 case and activation occurred 50 seconds earlier, correspondingly. Hence, the onset of activation is attributable to the temperature increase and not to the duration of incubation in the balanced pH solution.

Determination of Balanced pH of Activation Solutions

From the above experiments investigating activation triggering of encapsulated signal precursor under different pH and temperature conditions, the inventors noted that different capsule types required adjustment of the pH to a different value for achieving the desired balance. This is to be expected because different capsule types will have different permeabilities to the activating solution, different pore sizes, different wall thicknesses, etc. These are all factors that can affect the rate of hydrolysis of the signal precursor contained within the capsules. In addition, changing the signal precursor will most likely mean that hydrolysis occurs at a different pH. Therefore, for each combination of capsule type and signal precursor type, the balanced pH must be determined.

This is easily done by experiment:

For any chosen combination of capsule type and signal precursor type, a series of room temperature solutions of different pH is prepared and a portion of capsules is then added to each solution. The solutions are irradiated with excitation light and, if an intense signal is detected, the solution is noted as falling outside the balanced pH range. If no signal is detected, the solution is heated to 45° C. to 65° C. and again irradiated with excitation light. Heated solutions which emit an intense signal are noted as falling within the balanced pH range. Heated solutions which still do not emit a signal are noted as falling outside the balanced pH range.

If required, fine tuning can be carried out by preparing a series of solutions with small incremental changes to the pH within the pH range that has been noted the critical pH range from the first round of experiments described above.

In summary, the balanced pH may be determined by:
(a) adding a portion of capsules containing the signal precursor to a series of ambient temperature solutions of different pH;
(b) irradiating the series of ambient temperature solutions with excitation light;
(c) rejecting solutions that emit an intense signal at ambient temperature;
(d) heating the solutions that emit substantially no signal at ambient temperature;
(e) rejecting solutions that emit substantially no signal after heating, and
(f) noting the pH value of the solution or solutions that emit an intense signal after heating as defining the balanced pH.

Preferably, the activation or treatment solution is buffered to maintain its pH when it is mixed with other solutions in an assay system Preferably the pH of the balanced pH activation or treatment solution is too high by up to 0.5 for the signal precursor to undergo significant acid-catalysed hydrolysis to its signal generating form, or too low by up to 0.5 for the signal precursor to undergo significant base-catalysed hydrolysis to its signal generating form. More preferably, the pH of the activation or treatment solution is too high by up to 0.2 for the signal precursor to undergo significant acid-catalysed hydrolysis to its signal generating form, or too low by up to 0.2 for the signal precursor to undergo significant base-catalysed hydrolysis to its signal generating form. Even more preferably, the pH of the activation or treatment solution is too high by up to 0.1 for the signal precursor to undergo significant acid-catalysed hydrolysis to its signal generating form, or too low by up to 0.1 for the signal precursor to undergo significant base-catalysed hydrolysis to its signal generating form.

Temperature Range for Heating Step

In the experiments described above for determining the balanced pH for activation solutions, a temperature range of 45° C. to 65° C. is recited as the temperature to which the test solutions should be raised. 45° C. was chosen as the lowest "elevated" temperature to use because, in most geographic locations, this is well above ambient temperature and can therefore be distinguished from the unheated condition. Below 45° C., full activation can take a very long time, leading to the problem of signal dissipation which the present invention is intended to overcome. The upper limit of 65° C. was chosen because it is hot, but not too hot to touch by hand. Also, an even higher temperature may cause unwanted instability in the chemistry system. In addition, the inventors considered that it would be impractical for a simple handheld reader device to get so hot.

In the stated temperature range of 45° C. to 65° C., it is possible to achieve a measure of control over the time delay before the signal maximum is detected. This contributes to the versatility of the present invention.

Example Apparatus for Putting the Invention into Effect

Figure 14:
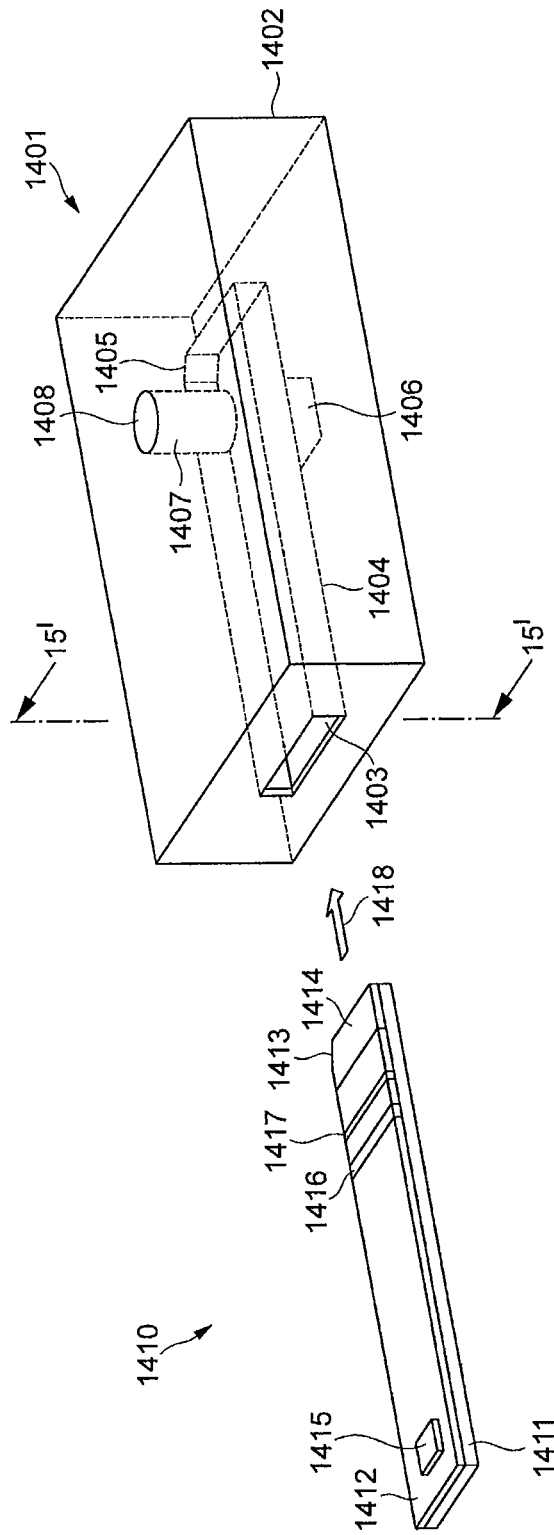
FIG. 14 is a schematic perspective view of a lateral flow test strip and a reader device adapted to receive the test strip.
Figure 15:
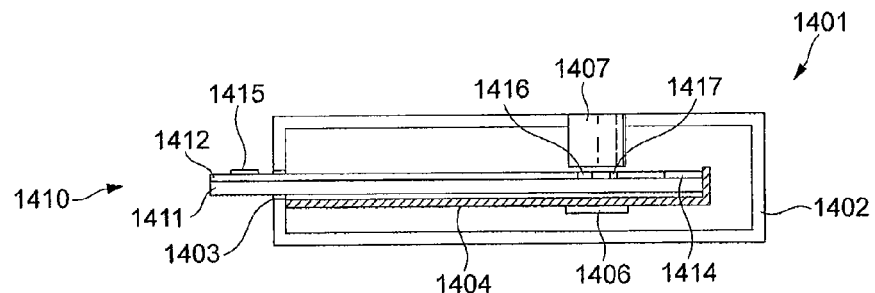
FIG. 15 is a schematic cross-sectional view of the reader shown in FIG. 14 taken on line 15'-15', and showing in profile the side of a test strip inserted fully into the reader.

Referring to FIGS. 14 and 15, there is shown an example of an apparatus for putting the invention into effect in a lateral flow test.

FIG. 14 is a schematic perspective view of a lateral flow test strip 1410 and a reader device 1401 that is adapted to receive the test strip 1410 and to process it as will be described in more detail below.

The reader 1401 comprises a housing 1402. At one end, the housing has a slot 1403 through which the test strip 1410 is insertable as indicated by arrow 1418. The slot leads to a tray 1404 provided in the interior space of the housing 1402, the tray serving as a guide for the test strip 1410 when it is inserted into the reader. Positioned below the tray is a heating device 1406 and above the tray, in register with the position of the heating device 1406, is the optical system 1407 for illuminating an inserted test strip with excitation light and for receiving and processing emitted light. The upper surface of the housing 1402 has an aperture or viewing window 1408 through which a readout from the optical system 1407 is viewable. The tray 1404 has a chamfered corner 1405.

The test strip 1410 comprises an impervious elongate support substrate 1411, which may be formed of a thermoplastic resin such as polyvinyl chloride, polypropylene or the like, on which is mounted a porous membrane 1412 formed of a bibulous material such as nitrocellulose or glass fiber capable of transporting an aqueous solution by capillary action, wicking, or simple wetting. The test strip 1410 has a cutaway corner 1413 which is configured to correspond to the chamfered corner 1405 of the tray 1404 in the reader 1401. This feature is intended to prevent the user from inserting the test strip 1410 into the reader 1401 the wrong way up because the test strip 1410 can only be inserted fully if the test strip is oriented such that its cutaway corner 1413 cooperates with the chamfered corner 1405 of the tray 1404.

At its end having the cutaway corner 1413, the test strip has a wicking pad 1414 which serves as a reservoir for accumulating fluids as they pass along the flow path defined by the porous membrane 1412 in the direction from left to right as shown in the drawing. The wicking pad 1414 may be, for example, a sorbent or supersorbent material comprising lightly cross-linked polyacrylate salts which are capable of absorbing many times their own weight in water. At or near the other end of the test strip 1410 there is a sample application zone 1415 on the porous membrane 1412 where a sample suspected of containing an analyte of interest is applied. The sample application zone 1415 is pre-loaded with capsules containing a signal precursor material, the capsules having on their surface affinity molecules for specific binding to the analyte that is to be detected.

Between the sample application zone 1415 and the wicking pad 1414 is a test zone 1416 where capture molecules are immobilized, the capture molecules also having the capability of binding specifically to the analyte that it is intended to detect. The capture molecules may be immobilized at the test zone 1416 using adsorption, absorption, or ionic or covalent coupling in accordance with methods that are well known in the art.

Downstream of the test zone 1416 is a control zone 1417 which includes non-specific capture molecules, i.e., capture molecules that do not bind specifically to the analyte but which are capable of binding to free capsules that flow past the test zone 1416. The control zone is not essential, but serves to confirm that the test has operated correctly, for example by indicating that the test strip has wetted correctly and that the flow of solutions has passed along the test strip from the sample application zone 1415 and through the test zone 1416.

Although the drawing shows the test zone 1416 and control zone 1417 as disposed serially along the flow path, test and control zones may alternatively be disposed side by side or in other special relationships.

The high sorptivity of the wicking pad 1414 promotes the flow of liquid along the test strip and ensures that solutions pass through the test zone 1416.

FIG. 15 is a schematic cross-sectional view of the reader 1401 taken on line 15'-15' in FIG. 14, but showing in profile the side of a test strip 1410 inserted fully into the tray 1404 via the slot 1403. The test strip 1410 is shown slightly elevated from the upper surface of the tray 1404 for clarity.

As can be clearly seen from this side-on view, the test zone 1416 and control zone 1417 of the fully inserted test strip 1410 overlie the heater device 1406 and are disposed directly below the optical system 1407.

Use of the apparatus illustrated in FIGS. 14 and 15 will now be described.

First, a solution of a test sample suspected of containing an analyte to be detected is applied to the sample application zone 1415 of the test strip 1410. The capsules that have been preloaded on the test strip in the sample application zone are taken up in the applied sample solution and interact with any analyte present through the intermediary of the affinity molecules on the capsule surface. As indicated previously, the affinity molecules bind specifically with the analyte.

The solution flows along the membrane 1412 in the direction from left to right as shown in the drawings, drawn by the action of the wicking pad 1414. Entrained in the solution are complexes formed between analyte molecules and the affinity molecules attached to the capsules, as well as free capsules having no analyte bound to them.

As they pass the capture molecules immobilized on the membrane in the test zone 1416, the complexes are removed from solution by interaction between the analyte and the capture molecules. Free capsules having no analyte bound to them continue in the solution flow, past the test zone and through the control zone.

A buffered wash solution may be applied to the membrane upstream of the test zone 1416 to ensure that free capsules having no analyte bound to them are washed beyond the test zone.

When the control zone 1417 shows that the test has operated correctly, a balanced pH treatment solution is applied to the membrane 1412 upstream of the test zone.

The balanced pH treatment solution may be applied to the membrane 1412 before the test strip 1410 is inserted into the reader 1401. Alternatively, the balanced pH treatment solution may be added after the test strip 1410 has been inserted into the reader 1401, in which case it is applied to the portion of the membrane 1412 that protrudes outside the reader 1401 (see FIG. 15).

Regardless of the order in which the test strip 1410 is inserted into the reader 1401 and the balanced pH treatment solution is applied to the membrane 1412, sufficient time is allowed for the balanced pH treatment solution to flow to the test zone 1416 before the heater device 1406 is actuated to cause an increase in the temperature of the volume of treatment solution above the location of the heater device. Since only small volumes of solution are involved in such tests, the increase in temperature of the treatment solution to an elevated setpoint value is very rapid.

Triggering of activation of the signal precursor within the capsules occurs within a few seconds or fractions of a second of the heating step and individual signal generating molecules are released from the capsules.

Next, the optical system 1407 is actuated. Excitation light, for example from an LED, is directed onto the test zone to cause the signal generating molecules to fluoresce and the emitted fluorescence is detected. A readout of the detected fluorescence is viewable through the viewing window 1408.

As indicated above, only small volumes of fluid are involved, so the device 1406 does not need to be very powerful. Equally, the optical system 1407 does not have a large energy demand, so the reader 1401 can be made self-contained by including a battery (not shown) within the housing 1402 to power the heater device 1406 and the optical system 1407. Alternatively, the reader can be externally powered.

Examples of Alternative Apparatus

In the example described above, the test strip 1410 was pre-loaded with capsules containing signal precursor material and having on their surface affinity molecules for specific binding to the analyte. Of course, it is possible instead to add the capsules to the sample of test solution prior to the application of the test solution to the sample application zone 1415.

Figure 16:
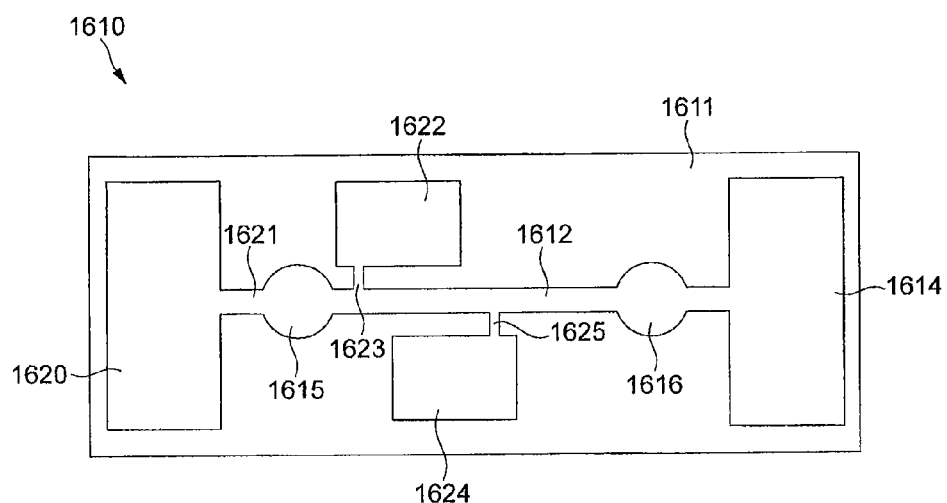
FIG. 16 is a schematic plan view of an alternative lateral flow test strip.
Figure 17:
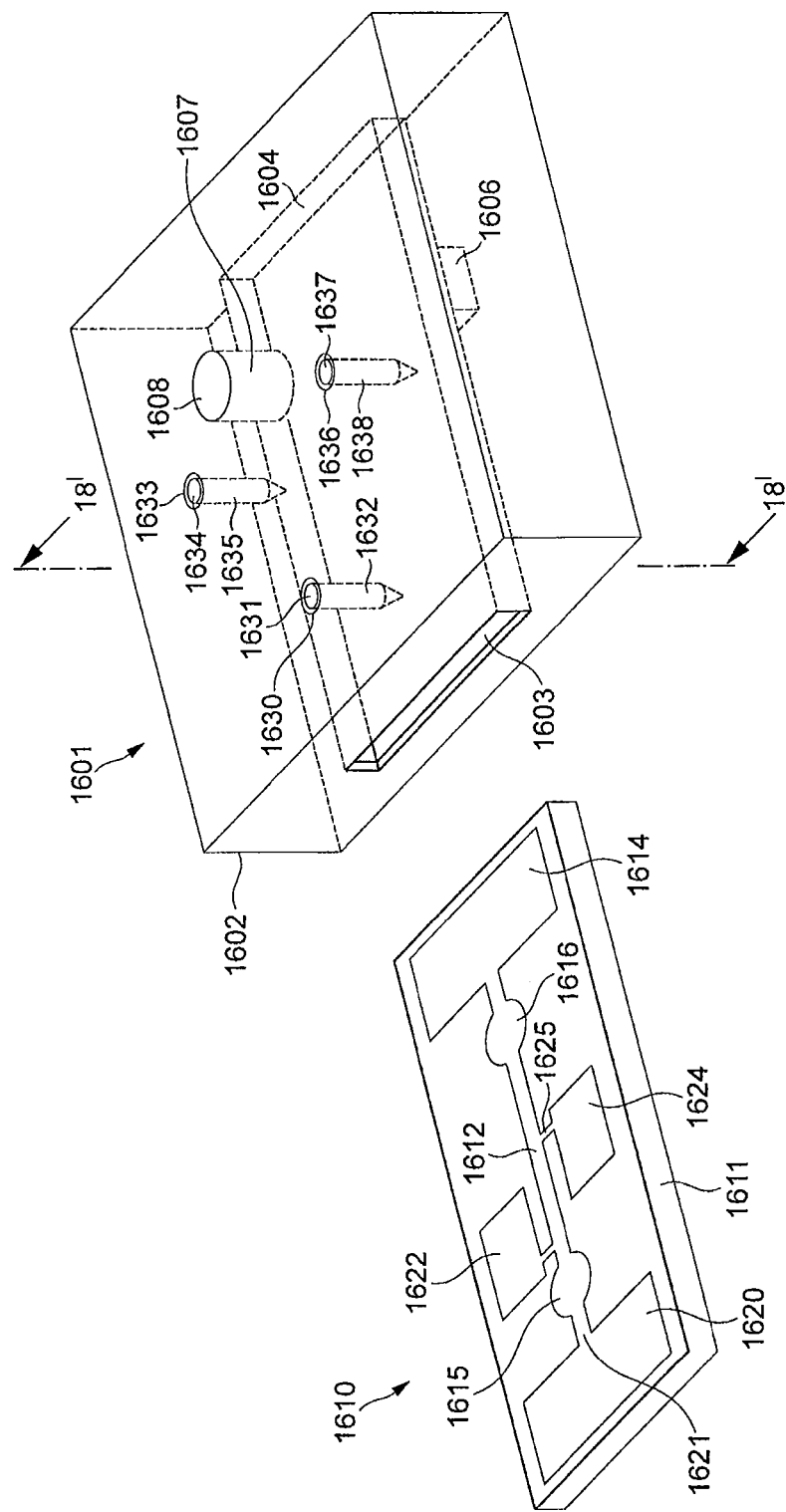
FIG. 17 is a schematic perspective view of the alternative lateral flow test strip of FIG. 16 and its associated reader apparatus.
Figure 18:
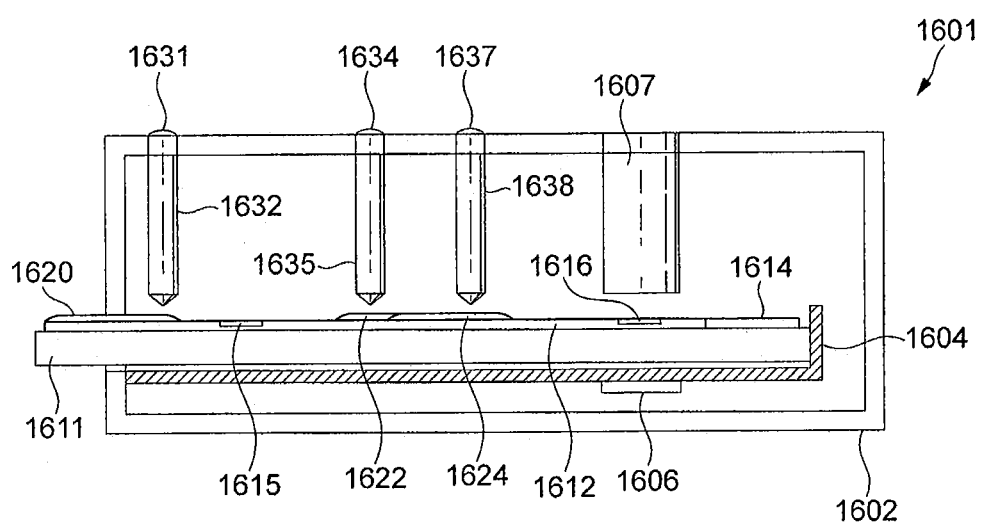
FIG. 18 is a schematic cross-sectional view of the reader shown in FIG. 17 taken on line 18'-18' and showing in profile the side of a test strip inserted fully into the reader.

Referring to FIGS. 16 to 18, there is shown an alternative form of apparatus for performing a lateral flow test where the test strip incorporates the solutions that are used in the test in rupturable reservoirs and where the reader has actuators for rupturing the reservoirs to release the solutions.

FIG. 16 is a schematic plan view of a test strip 1610 comprising a fluid impermeable barrier substrate 1611 which may be formed of a thermoplastic resin such as polyvinyl chloride, polypropylene or the like. A narrow strip of porous membrane 1612 formed of a bibulous material such as nitrocellulose or glass fiber is mounted on the substrate 1611. The porous membrane 1612 defines a fluid pathway for transporting aqueous solutions by capillary action, wicking, or simple wetting.

At its right-hand end as shown in the drawing, the test strip has a wicking pad 1614 that acts as a reservoir for accumulating fluids as they pass along the flow path defined by the porous membrane 1612 in the direction from left to right as shown in the drawing. The wicking pad 1614 may be, for example, a sorbent or supersorbent material capable of absorbing many times its own weight in water.

At the other end of the test strip 1610 there is a rupturable buffered carrier solution reservoir 1620 having a feed line 1621 at its right-hand edge. Just downstream of the feed line 1621 there is a sample application zone 1615 in fluid communication with the porous membrane 1612 four receiving a sample suspected of containing an analyte of interest. The sample application zone 1615 is pre-loaded with capsules containing a signal precursor material; the capsules have on their surface affinity molecules for specific binding to the analyte that is to be detected.

Downstream from the sample application zone 1615 is a second feed line 1623 connecting the porous membrane 1612 to a rupturable blocking agent reservoir 235. Further downstream is a third feed line 1625 connecting the porous membrane 1612 to a rupturable activation solution reservoir 1624.

Between the third feed line 1625 and the wicking pad 1614 is a test zone 1616 where capture molecules are immobilized, the capture molecules also having the capability of binding specifically to the analyte that it is intended to detect. The capture molecules may be immobilized at the test zone 1616 using adsorption, absorption, or ionic or covalent coupling in accordance with well-known methods.

Referring now to FIG. 17, here the test strip 1610 is shown in schematic perspective view in readiness for inserting into a reader apparatus 1601, also shown in schematic perspective view. The reader 1601 comprises a housing 1602 having a slot 1603 at its left-hand end as shown in the drawing for receiving the test strip 1610. The slot leads to a tray 1604 provided in the interior space of the housing 1602 that serves as a guide for the test strip 1610 when it is inserted into the reader. Positioned below the tray is a heating device 1606 and above the tray, in register with the position of the heating device 1606, is the optical system 1607 for illuminating an inserted test strip with excitation light and for receiving and processing emitted light. The upper surface of the housing 1602 has a viewing window 1608 through which a readout from the optical system 1607 is viewable.

The reader 1601 also has actuators 1632, 1633 and 1638 which are operable from the exterior of the housing upper surface to rupture respective ones of the rupturable reservoirs 1620, 1622 and 1624 on the test strip 1610, as will be described in more detail below. The actuator 1632 is provided with a button 1631 at its upper extremity that protrudes through the upper surface of the housing 1602. A concave depression 1630 surrounds the button. Similarly, actuator 1635 has a button 1634 at its upper extremity that is surrounded by a concave depression 1633 formed in the upper surface of the housing 1602. Likewise, actuator 1638 has a button 1637 at its upper extremity surrounded by a concave depression 1636 formed in the upper surface of the housing 1602.

FIG. 18 is a schematic cross-sectional view of the reader 1601 taken on line 18'-18' in FIG. 17, but showing in profile the side of a test strip 1610 inserted fully into the tray 1604 via the slot 1603. The test strip 1610 is shown slightly elevated from the upper surface of the tray 1604 for clarity.

As can be clearly seen from this side-on view, the test zone 1616 of the fully inserted test strip 1610 overlies the heater device 1606 and is disposed directly below the optical system 1607. Also, it can be seen that the actuator 1632 is disposed above the rupturable buffered carrier solution reservoir 1620, the actuator 1635 is disposed above the rupturable blocking agent reservoir 1622, and the actuator 1638 is disposed above the rupturable activation solution reservoir 1624.

Use of the apparatus illustrated in FIGS. 16 to 18 will now be described.

First, the test strip 1610 is inserted into the reader 1601 through the slot 1603. Then the actuator 1635 is used to rupture the rupturable blocking agent reservoir 1622 by pressing button 1634 downwards. This releases the blocking agent, which typically consists of PBS/BSA, and it flows to the porous membrane 1612 via the feed line 1623. The blocking agent flows along the porous membrane 1612 in a direction from left to right as shown in the drawing, drawn by the sucking power of the wicking pad 1614. The blocking agent passes over the test zone 1616 where capture molecules are immobilized. The blocking agent pre-wets and/or blocks reaction sites that are not loaded with capture molecules. This ensures that such reaction sites are neutralized so that they are unable to interact with a sample under test.

Then the test strip 1610 is retracted slightly from the reader 1601 to expose its sample application zone 1615. A solution of a test sample suspected of containing an analyte to be detected is then applied to the sample application zone 1615 and the test strip is re-inserted fully into the reader 1601. The capsules that have been preloaded on the test strip in the sample application zone are taken up in the applied sample solution and interact with any analyte present through the intermediary of the affinity molecules on the capsule surface. As indicated previously, the affinity molecules bind specifically with the analyte.

The solution flows along the membrane 1612 in the direction from left to right as shown in the drawings, drawn by the action of the wicking pad 1614. Entrained in the solution are complexes formed between analyte molecules and the affinity molecules attached to the capsules, as well as free capsules having no analyte bound to them.

Next, the actuator 1632 is used to rupture the rupturable buffered carrier solution reservoir 1620 by pressing button 1631 downwards. This releases the buffered carrier solution which flows to the porous membrane 1612 via the feed line 1621. The buffered carrier solution flows along the porous membrane 1612 in a direction from left to right as shown in the drawing, drawn by the sucking power of the wicking pad 1614, and carries the complexes formed between analyte molecules and the affinity molecules attached to the capsules, as well as free capsules, to the test zone.

As they pass the capture molecules immobilized on the membrane in the test zone 1616, the complexes are removed from solution by interaction between the analyte and the capture molecules. The buffered carrier solution washes any free capsules having no analyte bound to them beyond the test zone.

Next, the actuator 1638 is used to rupture the activation solution reservoir 1624 by pressing button 1637 downwards. The activation solution reservoir contains a balanced pH activation solution. When the reservoir 1624 is ruptured, this releases the balanced pH activation solution which flows to the porous membrane 1612 five the feed line 1625. The balanced pH activation solution flows along the porous membrane 1612 in a direction from left to right as shown in the drawing, drawn by the sucking power of the wicking pad 1614.

Sufficient time is allowed for the balanced pH activation solution to flow to the test zone 1616 before the heater device 1606 is turned on to cause an increase in the temperature of the volume of activation solution above the location of the heater device. Since only a small volume of solution is present in the porous membrane 1612 above the heater device 1606, the increase in temperature of the activation solution to an elevated setpoint value is very rapid.

Triggering of activation of the signal precursor within the capsules occurs within a few seconds or fractions of a second of the heating step and individual signal generating molecules are released from the capsules.

Next, the optical system 1607 is actuated. Excitation light, for example from an LED, is directed onto the test zone to cause the signal generating molecules to fluoresce and the emitted fluorescence is detected. A readout of the detected fluorescence is viewable through the viewing window 1608.

In a variant of the above method, the step of blocking reaction sites that are not loaded with capture molecules using a blocking agent can be omitted if test strips are pre-treated with a blocking solution before distribution to end users. In these circumstances, the test strip does not need to include a rupturable blocking agent reservoir and the solution test sample can be applied to the sample application zone 1615 before the test strip 1610 is first inserted into the reader 1601.

Heater Variants

Various types of heater device may be used to achieve the desired heating of the activation solution to trigger activation, including but not restricted to resistive, radiant, microwave, or inductive heating devices. Another example is a Peltier device such as used in the experiments described above for investigating the behaviour of signal precursor-containing capsules under different pH and temperature conditions. It is also possible to heat the activation solution through the application of ultrasound.

Capsule Behaviour after Triggering Activation and Capsule Variants

The fate of the capsule walls of the triggering activation does not appear to affect the performance of buyer assays. In WO02/12888 A2 it was reported that the capsules disintegrated, but now better understanding of the capsule behaviour has been achieved and it is known that certain types of capsule remain intact after the signal precursor has been activated the signal generating molecules released from encapsulation.

If the capsule wall is a surfactant, then hydrolysis of the encapsulated precursor material results in either an empty surfactant capsule, equivalent to a micelle, by the hydrolyzed signal generating molecules diffusing out, or the capsule falls apart due to the concentration of the surfactants being lower than the critical micelle concentration.

On the other hand, if the capsule wall is a surfactant coupled with a polymer, then the capsule may remain intact. See Caruso, F. Langmuir 2000, 16, 1485-1488.

Surfactants that may be used in the preparation of capsules for encapsulating signal precursors in connection with the present invention include:

(i) Cationic Surfactants:

DSPE-PEG(2000) Amine Benzalkonium chloride, Benzethonium chloride, Bronidox, Cetyltrimethylammonium bromide (CTAB), Cetyltrimethylammonium chloride, Dimethyldioctadecylammonium chloride, Lauryl methyl gluceth-10 hydroxypropyl dimonium chloride, Tetramethylammonium hydroxide.

(ii) Anionic Surfactants:

Ammonium lauryl sulfate, Dioctyl sodium sulfosuccinate, Perfluorobutanesulfonic acid, Perfluorononanoic acid, Perfluorooctanesulfonic acid, Perfluorooctanoic acid, Potassium lauryl sulfate, Sodium dodecyl sulfate, Sodium dodecylbenzenesulfonate, Sodium laureth sulfate, Sodium lauroyl sarcosinate, Sodium myreth sulfate, Sodium palmate, Sodium pareth sulfate, Sodium stearate, Sodium tallowate.

(iii) Zwitterionic Surfactants:

Amphiphile, CHAPS detergent, Cocamidopropyl betaine, Cocamidopropyl hydroxysultaine, Hydroxysultaine, Lecithin, Sodium lauroamphoacetate.

(iv) Non-Ionic Surfactants:

Cetomacrogol 1000, Cetostearyl alcohol, Cetyl alcohol, Cocamide DEA, Cocamide MEA, Decyl glucoside, Glyceryl laurate, Isoceteth-20, Lauryl glucoside, Narrow range ethoxylate, Nonidet P-40 (Registered Trade Mark), Nonoxynol-9, Nonoxynols, NP-40, Octaethylene glycol monododecyl ether, Octyl glucoside, Oleyl alcohol, Pentaethylene glycol monododecyl ether, Poloxamer, Poloxamer 407, Polyglycerol polyricinoleate, Polysorbate, Polysorbate 20, Polysorbate 80, Sorbitan monostearate, Sorbitan tristearate, Stearyl alcohol, Triton X-100 (Registered Trade Mark)l.

(v) Polar Uncharged Molecules:

Sterols, carbohydrates, etc.

Polymers that may be used in the preparation of capsules for encapsulating signal precursors in connection with the present invention include:

(vi) Basic Polymers:

PAH poly(allylamine hydrochloride), PVP (Polyvinyl pyrrolidone), PEI (Polyethylenimine), PEG (Polyethylene glycol), polylysine, polypeptides including histones, ribosomal protein, protamine, (vii) Acidic Polymers:

PSS poly(sodium 4-styrenesulfonate), polyglutamate, polyaspartate, nucleic acids, etc.

Capsules may also be prepared using combinations of surfactants and polymers.

Other Variants of Bioassay

In the foregoing, a bioassay procedure has been described with reference to FIG. 1 in which, in the first step, a test sample suspected of containing the analyte 10 is mixed in solution with capsules 20 containing signal precursor material 30. It is of course well understood that this does not necessarily have to be the first step in carrying out a bioassay. Alternative procedures will now be described briefly with reference to FIGS. 19 to 22.

Figure 19:
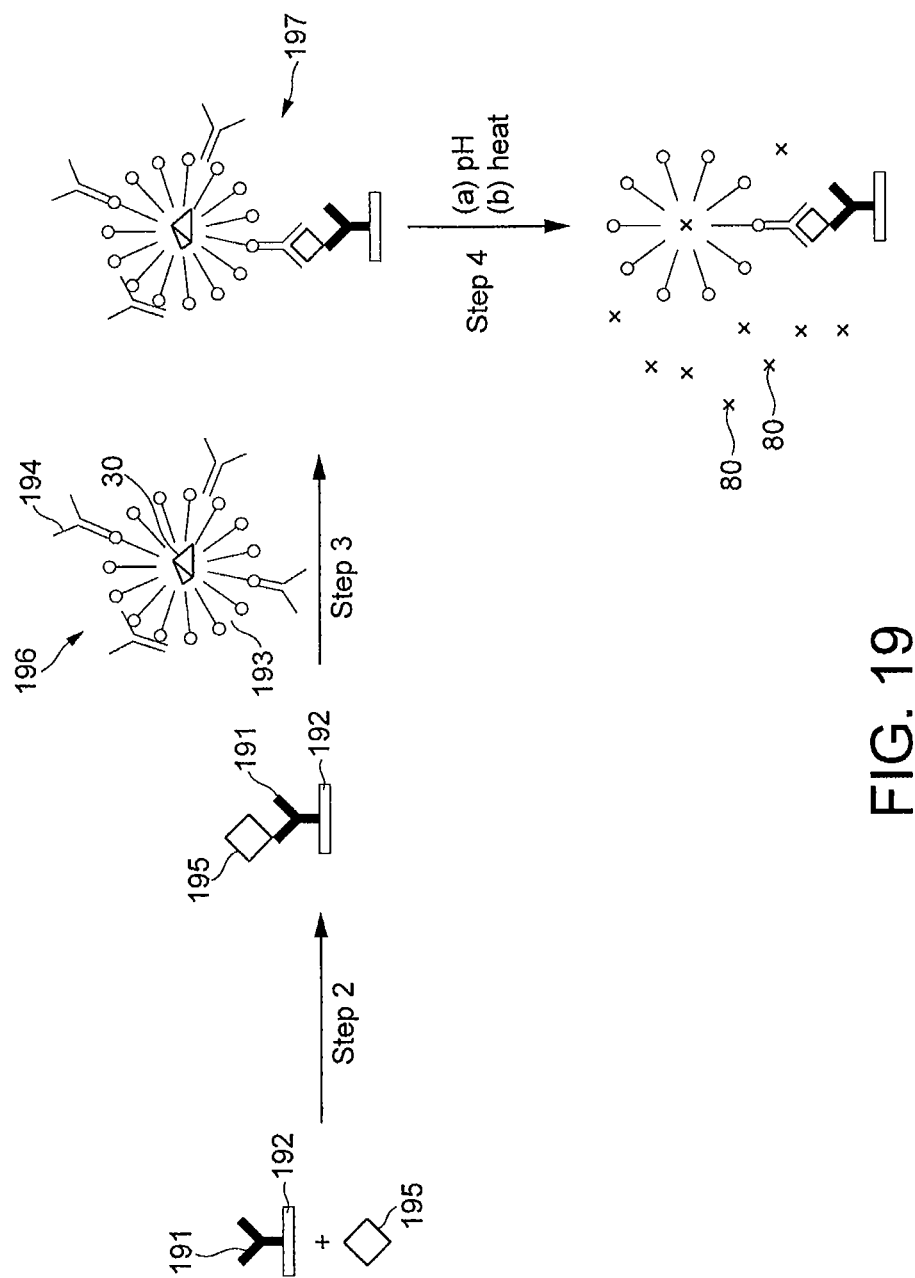
FIG. 19 is a diagram showing a sequence of steps for an alternative immunoassay using capsules containing a signal precursor.

FIG. 19 is a diagram showing a sequence of steps for performing an immunoassay using capsules containing a signal precursor.

A device is used comprising a specific capture antibody 191 immobilised on a substrate 192. The capture antibody 191 immobilised on the substrate 192 could, for example, correspond to the immobilised capture molecules in a test zone in a lateral flow test apparatus such as described above in connection with FIGS. 14 to 18. The capture antibody 191 has an affinity for, and is able to bind specifically to, an antigen 195 which is the target species to be detected in the immunoassay.

In a first step (not shown) the substrate 192 with the capture antibody 191 immobilised on its surface is pre-wetted and/or blocked by treatment with a solution of bovine serum albumin in phosphate buffered saline (PBS/BSA) to ensure that any reactive sites on the substrate 192 are neutralised so that they are unable to interact with the later-applied antigen. Unblocked reactive sites might otherwise result in false readings.

In the second step, shown in the top left of the drawing, a solution suspected of containing the antigen 195 is flowed over the device. If the antigen is present, at least some of it will be captured by becoming bound to the capture antibody 191. For the sake of simplicity, FIG. 19 shows a single antigen 195 becoming bound to a single capture antibody 191. In practice, the capture zone of the device will have many capture antibodies 191 immobilised on the substrate 192 and any one of these capture antibodies will be capable of binding to an antigen 195. Each of the capture antibodies 191 is only capable of binding to a single antigen 195 because of the highly specific nature of antibody/antigen binding site geometry.

In the third step, a solution of capsules 193 containing signal precursor 30 and having affinity molecules on their surface in the form of antibodies 194 is flowed over the device. Like capture antibodies 191, the antibodies 194 on the surface of the capsules 193 have an affinity for, and also able to bind specifically to, the antigen 195. For convenience, the capsules having antibodies 194 on their surface will be referred to as Ab-coupled capsules 196. By virtue of the antibodies 194 acting as the affinity molecules of the capsules 193, and by virtue of the affinity of the antibodies 194 for the antigen 195, the Ab-coupled capsules 196 become bound to the antigens 195 that have been captured by the capture antibodies 191. There is thus formed a captured complex 197.

In the fourth step, the device with its captured complexes 197 is washed to remove any uncaptured Ab-coupled capsules and then a treatment solution of balanced pH is applied to the device. After a desired incubation period, the treatment solution is heated to effect triggering of activation of the capsules. The signal precursor 30 is hydrolysed and released from the capsules in the form of individual molecules 80 of signal generating substance.

In a final step (not shown) the signal generating molecules 80 are irradiated with excitation light and the emitted light (generated signal) is detected and measured.

Figure 20:
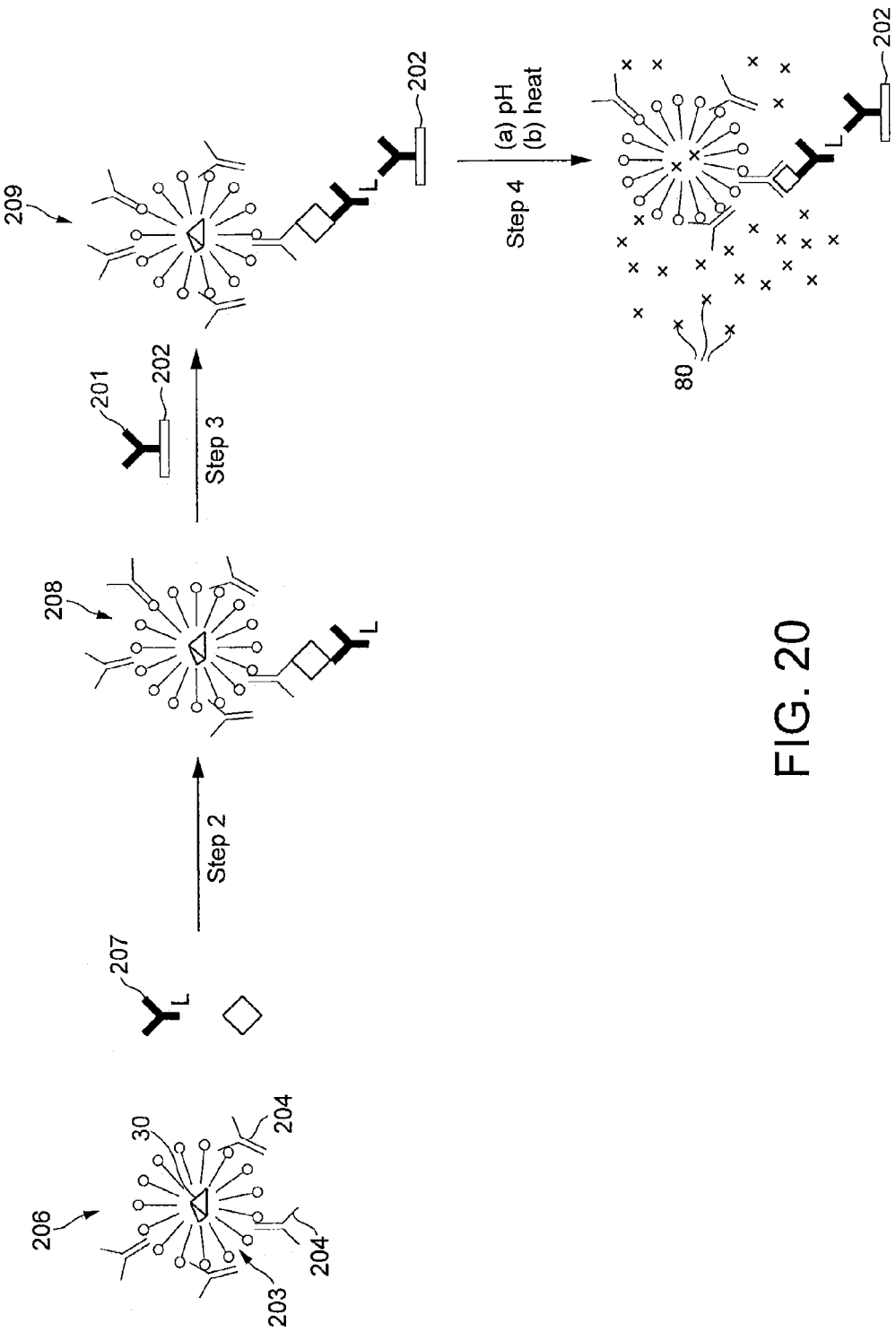
FIG. 20 is a diagram showing parts of another alternative scheme for performing an immunoassay using capsules containing a signal precursor.

FIG. 20 is a diagram showing parts of another alternative scheme for performing an immunoassay using capsules containing a signal precursor.

In this alternative scheme, a labelled detection antibody 207 is used that binds to a capture antibody 201 immobilised on a substrate 202 of a detection device. By using a suitable label (denoted in the drawing by subscript L) that is capable of binding to the capture antibody 201, the same capture antibody 201 can be used for many different assays because the assay specificity derives from the detection antibody 207.

In a first step (not shown) the substrate 202 with the capture antibody 201 immobilised on its surface is pre-wetted and/or blocked by treatment with a solution of bovine serum albumin in phosphate buffered saline (PBS/BSA) to ensure that any reactive sites on the substrate 202 are neutralised so that they are unable to interact with the later-applied antigen. Unblocked reactive sites might otherwise lead to false readings.

In the second step, a solution suspected of containing an antigen 205 is pre-mixed with Ab-coupled capsules 206 and labelled detection antibodies 207. The Ab-coupled capsules 206 are formed from capsules 203 that contain a signal precursor 30, with affinity molecules in the form of antibodies 204 on their surface. The antibodies are capable of binding to the antigen 205. Likewise, the labelled detection antibodies 207 are also capable of binding to the antigen 205. This pre-mixing step results in the formation of a sandwich complex 208 when antigen 205 is present. The antigen 205 becomes "sandwiched" between one of the antibodies 204 of the Ab-coupled capsule 206 and one of the labelled detection antibodies 207.

In the next step, the pre-mixed solution of sandwich complexes 208 is flowed over the device. By virtue of the affinity of the labels L of the labelled detection antibodies 207 for the immobilised capture antibodies 201, the sandwich complexes 208 become captured as a captured complex 209.

In the fourth step, the device with its captured complexes 209 is washed to remove any uncaptured sandwich complexes 208. After washing, a balanced pH activation solution is applied to the device and then, after the desired incubation period, the activation solution is heated to effect triggering of activation of the capsules. The signal precursor 30 is hydrolysed and released from the capsules in the form of individual molecules 80 of signal generating substance.

In a final step (not shown) the signal generating molecules 80 are irradiated with excitation light and the emitted light (generated signal) is detected and measured.

The scheme depicted in FIG. 20 has the following, requirements. Firstly, the capture antibody 201 is immobilised on the substrate 202. This can be done by chemical coupling or alternatively by allowing the capture antibody to become adsorbed directly onto a plastic substrate such as polystyrene. Secondly, the capsules 203 have to be coupled to antibodies 204 as the affinity molecules that are capable of binding to the target to be detected. Thirdly, an antibody that is specific to label "L" is required that must also be capable of binding to the target to be detected. The label "L" can be any commonly available conjugate to an antibody, for example DNP, digoxin, or various dyes.

Figure 21:
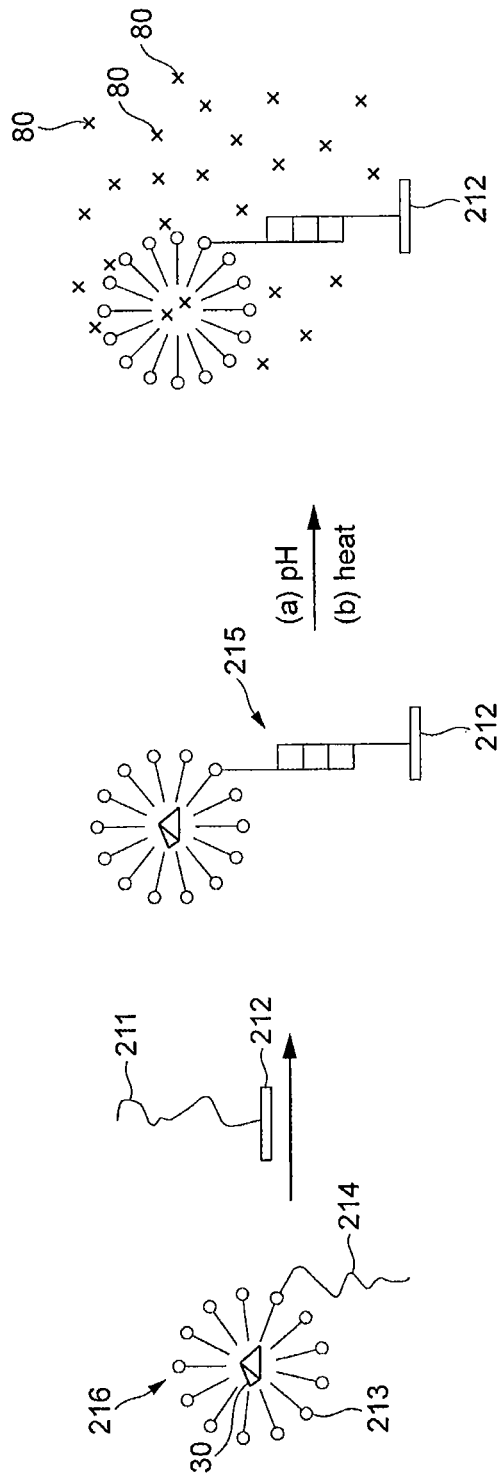
FIG. 21 is a diagram showing parts of yet another alternative scheme for performing a hybridisation assay using capsules containing a signal precursor.

FIG. 21 is a diagram showing parts of yet another alternative scheme for performing a hybridisation assay using capsules containing a signal precursor. In this scheme, the detection device has a nucleic acid fragment (oligonucleotide) 211 immobilised on a substrate 212. The nucleic acid fragment 211 functions in much the same way as the capture antibodies 191 and 201 described above in connection with FIGS. 19 and 20 and, like those capture antibodies, could be considered as an example of a capture molecules in a capture zone of a lateral flow test device such as described above in connection with FIGS. 14 to 18.

In a first step (not shown), the substrate 212 with the oligonucleotide 211 immobilised on its surface is pre-wetted and/or blocked by treatment with a solution of bovine serum albumin in phosphate buffered saline (PBS/BSA) to ensure that any reactive sites on the substrate 212 are neutralised so that they are unable to interact with the later-applied target solution containing complimentary nucleic acid sequences because unblocked reactive sites might be the cause of false readings.

In a separate step, a solution of capsules 213 containing signal precursor is prepared, the capsules 213 being conjugated to oligonucleotides 214 that are to be detected. For convenience, the capsules conjugated to oligonucleotides will be referred to as nucleic acid complexes 216.

The next step is shown in the drawing; the solution of nucleic acid complexes 216 is flowed over the device. Those complexes 216 having an oligonucleotide 214 that is complimentary to the immobilised oligonucleotide 211 on the substrate 212 will become captured by hybridisation of the two complimentary oligonucleotides 211 and 214, thus forming captured complexes 215. The device with its captured complexes 215 is washed to remove any uncaptured nucleic acid complexes 216.

In the second step shown in the drawing, a balanced pH activation solution is applied to the device and then, after the desired incubation period, the activation solution is heated to effect triggering of activation of the capsules. The signal precursor 30 is hydrolysed and released from the capsules in the form of individual molecules 80 of signal generating substance.

In a final step (not shown) the signal generating molecules 80 are irradiated with excitation light and the emitted light (generated signal) is detected and measured.

The hybridisation scheme depicted in FIG. 21 has the following requirements. Firstly, the oligonucleotides 211 are immobilised on the substrate 212. This requires some form of chemical coupling and control over directionality such that the 5'-3' direction is the same for each immobilised oligonucleotide and the opposite direction from how the oligonucleotides 214 are immobilised on the capsules 213. Secondly, the oligonucleotides 214 are conjugated to the capsules 213, again with controlled directionality. Thirdly, the oligonucleotides 211 must have complementarity for the oligonucleotides 214 that are to be detected.

Figure 22:
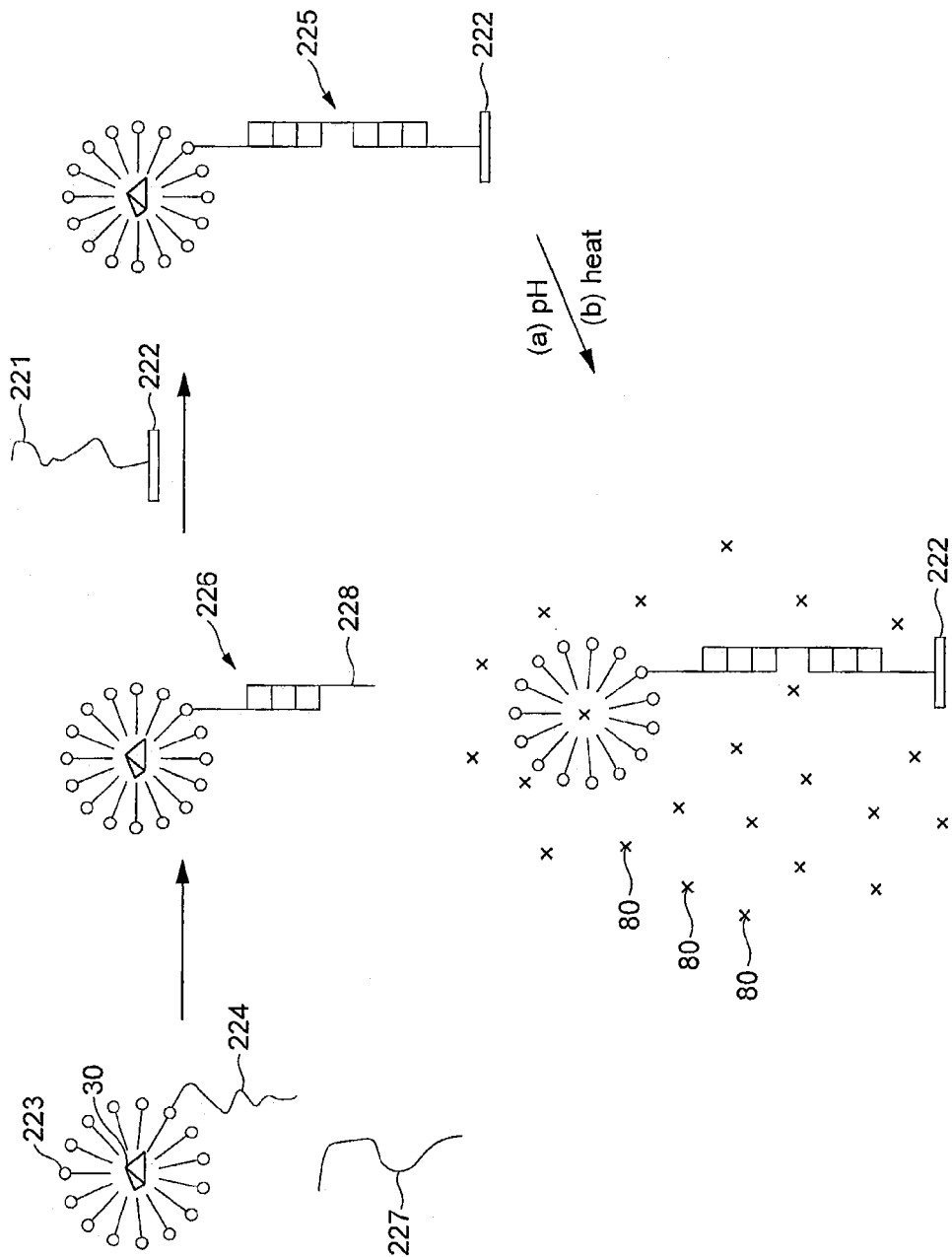
FIG. 22 is a diagram showing parts of another scheme for performing a hybridisation assay using capsules containing a signal precursor.

FIG. 22 is a diagram showing parts of another scheme for performing a hybridisation assay using capsules containing a signal precursor.

In this scheme, the detection device has a first nucleic acid fragment (oligonucleotide) 221 immobilised on a substrate 222, much the same as the device used in the hybridisation scheme depicted in FIG. 21. Hence, the oligonucleotide 221 could be considered as an example of a capture molecule used in the test zone of a lateral flow test device such as described above in connection with FIGS. 14 to 18.

As before, the detection device comprising the first oligonucleotides 221 immobilised on the substrate 222 is pre-wetted and/or blocked by treatment with PBS/BSA to ensure that any reactive sites on the substrate 222 are neutralised to, eliminate false readings.

In the first step shown in the drawing, a solution is prepared of capsules 223 containing signal precursor, the capsules 223 being conjugated to oligonucleotides 224 that are to be detected. To this is handed a solution containing the third nucleic acid fragment (oligonucleotide) which will be referred to here as a "bridge" oligonucleotide 227. The bridge oligonucleotides 227 hybridise with the oligonucleotides 224 conjugated to the capsules 223, forming bridge oligonucleotide complexes 226 that have a tail 228 that is capable of further hybridisation.

In the next step, the solution of bridge oligonucleotide complexes 226 is flowed over the device. The tails 228 of the complexes 226 are complimentary to the immobilised oligonucleotides 221 on the substrate 222 and therefore further hybridisation takes place and the complexes 226 become captured on the device by this further hybridisation, forming captured complexes 225. The device with its captured complexes 225 is washed to remove any uncaptured nucleic acid complexes 226.

In the next step, a balanced pH activation solution is applied to the device and then, after the desired incubation period, the activation solution is heated to effect triggering of activation of the capsules. The signal precursor 30 is hydrolysed and released from the capsules in the form of individual molecules 80 of signal generating substance.

In a final step (not shown) the signal generating molecules 80 are irradiated with excitation light and the emitted light (generated signal) is detected and measured.

The hybridisation scheme depicted in FIG. 22 has the following requirements. Firstly, the oligonucleotides 221 have to be immobilised on the substrate 222. This requires some form of chemical coupling and control over directionality such that the 5'-3' direction is the same for each immobilised oligonucleotide and the same as the 5'-3' direction of the oligonucleotides 224 conjugated to the capsules 223. Secondly, the oligonucleotides 224 have to be conjugated to the capsules 223, again with controlled directionality. Thirdly, the oligonucleotides 221 must have complementarity for the bridging oligonucleotides 227 which must themselves have complementarity for the oligonucleotides 224 that are to be detected.

Examples of Different Affinity Molecule Types for Use on the Capsules and their Methods of Conjugation Depending on the target molecules to be detected, the affinity molecules may be biorecognition molecules selected from the following groups of materials:
(a) peptides or proteins selected from the group consisting of antibodies, genetically modified antibodies, monoclonal antibodies, polyclonal antibodies, receptors, antigens, lectins, avidins, oligopeptides, lipoproteins, glycoproteins, peptide hormones and allergens or parts thereof;
(b) nucleic acids selected from the group consisting of DNA, RNAs, oligonucleotides, aptamers and parts thereof;
(c) carbohydrates selected from the group consisting of mono-, oligo- and polysaccharides, glycolipids, proteopolysaccharides and parts thereof; or
(d) low molecular weight ligands selected from the group consisting of biotin, biotin derivatives, steroids, hormones, cofactors, activators, inhibitors, drugs, allergens or haptens.

The affinity molecules may be conjugated to the outer surface of the capsules, for example. by van der Waals forces, hydrogen bonds or electrostatic interactions, or they may be covalently bound to the outer surface of the capsules directly or via linker molecules. The linker molecule is usually a biomolecule, preferably avidin, streptavidin, neutravidin, protein A, protein G, lectin or a low molecular crosslinker.

Although the invention has been described above with reference to particular embodiments and examples, these are non-limiting and it will be understood by person skilled in the art that other variations and modifications are possible without departing from the scope of the invention as defined by the following claims.

What is claimed is:
1. A method of controlling the onset of signal generation in a bioassay using capsules containing a signal precursor that is hydrolysable from a latent form in which substantially no signal is generated to a form in which it is able to generate a detectable signal, the method comprising:
(i) treating the capsules with a solution whose temperature is such that substantially no hydrolysis of the signal precursor takes place and whose pH is balanced such that either:
(a) the pH is too high for the signal precursor to undergo significant acid-catalysed hydrolysis at ambient temperature but at which the signal precursor undergoes significant hydrolysis at elevated temperature; or:
(b) the pH is too low for the signal precursor to undergo significant base-catalysed hydrolysis at ambient temperature but at which the signal precursor undergoes significant hydrolysis at elevated temperature; and
(ii) subsequently heating the capsules in the treatment solution to initiate onset of hydrolysis of the signal precursor to the form in which it is able to generate a detectable signal.

2. A method of controlling the onset of signal generation in a bioassay using capsules containing a signal precursor that is hydrolysable from a latent form in which substantially no signal is generated to a form in which it is able to generate a detectable signal, the method comprising:
(i) treating the capsules with a balanced pH treatment solution whose temperature is such that substantially no hydrolysis of the signal precursor takes place and whose balanced pH has been pre-determined by:
(a) adding a portion of capsules containing the signal precursor to a series of ambient temperature solutions of different pH;
(b) irradiating the series of ambient temperature solutions with excitation light;
(c) rejecting solutions that emit an intense signal at ambient temperature;
(d) heating the solutions that emit substantially no signal at ambient temperature;
(e) rejecting solutions that emit substantially no signal after heating, and
(f) noting the pH value of the solution or solutions that emit an intense signal after heating as defining the balanced pH; and
(ii) subsequently heating the capsules in the treatment solution to initiate onset of hydrolysis of the signal precursor to the form in which it is able to generate a detectable signal.

3. The method of claim 1 or claim 2 wherein the step of subsequently heating the capsules in the treatment solution comprises heating the treatment solution to a temperature in the range from 40° C. to 75° C.

4. The method of claim 1 or claim 2 wherein the step of subsequently heating the capsules in the treatment solution comprises heating the treatment solution to a temperature in the range from 45° C. to 65° C.

5. The method of claim 1 or claim 2 wherein the step of subsequently heating the capsules in the treatment solution comprises heating the treatment solution using a heating device selected from the group consisting of a resistive heating device, a radiant heating device, a microwave heating device, an inductive heating device and a Peltier device.

6. The method of claim 1 or claim 2 wherein the step of subsequently heating the capsules in the treatment solution comprises heating by ultrasound.

7. The method of claim 6 wherein the ultrasound is low-frequency ultrasound in the range from 20 to 60 KHz.

8. The method of claim 6 wherein the ultrasound is high-frequency ultrasound in the range from 1 to 8 MHz.

9. The method according to claim 1 or claim 2 wherein the step of subsequently heating the capsules in the treatment solution is carried out after an interval from 100 seconds to 500 seconds following addition of the treatment solution to the capsules.

10. The method according to claim 1 or claim 2 wherein the signal generating substance contained in the capsules is an organic material.

11. The method according to claim 1 or claim 2 wherein the capsules contain from $10^7$ to $10^9$ molecules of the signal precursor per capsule.

12. The method according to claim 1 or claim 2 wherein the signal precursor is selected from the group consisting of hydrolysable fluorophores, hydrolysable luminophores, hydrolysable chromophores, hydrolysable bioluminogenic proteins and hydrolysable fluorogenic proteins.

13. The method according to claim 12 wherein the signal precursor is a hydrolysable fluorophore.

14. The method according to claim 12 wherein the signal precursor is fluorescein diacetate.

15. A method of performing a bioassay for detection of one or more target molecules in a sample, the method comprising:
(i) attaching a plurality of capture molecules on a substrate, the capture molecules having an affinity for the target molecules;
(ii) mixing the sample in solution with capsules containing a signal precursor that is hydrolysable from a latent form in which substantially no signal is generated to a form in which it is able to generate a detectable signal, the capsules carrying on their outer surface affinity molecules for specific recognition of and binding to any target molecules in the sample to enable formation of target-capsule complexes;
(iii) contacting the solution with the capture molecules on the substrate and allowing any target-capsule complexes to bind with the capture molecules;
(iv) separating capsules that are not complexed with target molecules from any target-capsule complexes bound to the capture molecules;
(v) treating any target-capsule complexes bound to the capture molecules with a treatment solution whose temperature is such that substantially no hydrolysis of the signal precursor takes place and whose pH is balanced such that either:
(a) the pH is too high for the signal precursor to undergo significant acid-catalysed hydrolysis at ambient temperature but at which the signal precursor undergoes significant hydrolysis at elevated temperature, or:
(b) the pH is too low for the signal precursor to undergo significant base-catalysed hydrolysis at ambient temperature but at which the signal precursor undergoes significant hydrolysis at elevated temperature;
(vi) heating any target-capsule complexes bound to the capture molecules in the balanced pH treatment solution, the heating causing hydrolysis of the signal precursor contained in the capsules to the form that is able to generate a signal;
(vii) irradiating the balanced pH treatment solution with excitation light in the vicinity of the capture molecules on the substrate, and
(viii) detecting any generated signal.

16. The method of performing a bioassay according to claim 15 wherein the step of heating any target-capsule complexes bound to the capture molecules in the balanced pH treatment solution comprises heating the treatment solution to a temperature in the range from 40° C. to 75° C.

17. The method of performing a bioassay according to claim 15 wherein the step of heating any target-capsule complexes bound to the capture molecules in the balanced pH treatment solution comprises heating the treatment solution to a temperature in the range from 45° C. to 65° C.

18. The method of performing a bioassay according to claim 15 wherein the step of heating any target-capsule complexes bound to the capture molecules in the balanced pH treatment comprises heating the treatment solution using a heating device selected from the group consisting of a resistive heating device, a radiant heating device, a microwave heating device, an inductive heating device and a Peltier device.

19. The method of performing a bioassay according to claim 15 wherein the step of heating any target-capsule complexes bound to the capture molecules in the balanced pH treatment solution comprises subjecting the treatment solution to low-frequency ultrasound in the range from 20 to 60 kHz.

20. The method of performing a bioassay according to claim 15 wherein the step of heating any target-capsule complexes bound to the capture molecules in the balanced pH treatment solution comprises subjecting the treatment solution to high-frequency ultrasound in the range from 1 to 8 MHz.

21. The method of performing a bioassay according to claim 15 wherein the step of heating any target-capsule complexes bound to the capture molecules in the balanced pH treatment solution is carried out after an interval from 100 seconds to 500 seconds following addition of the treatment solution to the capsules.

22. The method of performing a bioassay according to claim 15 wherein the signal precursor contained in the capsules is selected from hydrolysable fluorophores, hydrolysable luminophores, hydrolysable chromophores, hydrolysable bioluminogenic proteins and hydrolysable fluorogenic proteins.

23. The method of performing a bioassay according to claim 22 wherein the signal precursor is a hydrolysable fluorophore.

24. The method of performing a bioassay according to claim 23 wherein the signal precursor is fluorescein diacetate.

* * * * *